United States Patent
Baker et al.

(10) Patent No.: US 7,459,446 B2
(45) Date of Patent: *Dec. 2, 2008

(54) TREATMENT OF DIABETES WITH COPPER BINDING COMPOUNDS

(76) Inventors: John Richard Baker, PO Box 2165, Auckland (NZ); Garth J. S. Cooper, PO Box 147-091, Auckland (NZ)

( * ) Notice: Subject to any disclaimer, the term of this patent is extended or adjusted under 35 U.S.C. 154(b) by 0 days.

This patent is subject to a terminal disclaimer.

(21) Appl. No.: 11/023,827

(22) Filed: Dec. 28, 2004

(65) Prior Publication Data

US 2005/0159489 A1     Jul. 21, 2005

Related U.S. Application Data

(63) Continuation of application No. 10/226,685, filed on Aug. 23, 2002, now Pat. No. 6,897,243, which is a continuation of application No. 09/975,751, filed on Oct. 10, 2001, now Pat. No. 6,610,693, which is a continuation of application No. 09/671,967, filed as application No. PCT/NZ99/00161 on Sep. 24, 1999, now Pat. No. 6,348,465.

(30) Foreign Application Priority Data

Sep. 25, 1998 (NZ) ..................... 332084
Sep. 28, 1998 (NZ) ..................... 332079
Mar. 3, 1999 (NZ) ..................... 334471
Aug. 9, 1999 (NZ) ..................... 337042

(51) Int. Cl.
*A61K 31/33* (2006.01)
*A61K 31/415* (2006.01)
*A61K 31/195* (2006.01)
*A61K 31/13* (2006.01)

(52) U.S. Cl. .............. 514/183; 514/400; 514/561; 514/562; 514/674

(58) Field of Classification Search ........... 514/183, 514/400, 561, 562, 674
See application file for complete search history.

(56) References Cited

U.S. PATENT DOCUMENTS

| | | |
|---|---|---|
| 3,791,988 A | 2/1974 | Dieter |
| 4,323,558 A | 4/1982 | Nelson |
| 4,374,829 A | 2/1983 | Harris et al. |
| 4,410,541 A | 10/1983 | Kamimae et al. |
| 4,758,583 A | 7/1988 | Cerami et al. |
| 4,866,090 A | 9/1989 | Hoffman et al. |
| 4,952,568 A | 8/1990 | Sawai et al. |
| 5,077,313 A | 12/1991 | Lubec |
| 5,128,360 A | 7/1992 | Cerami et al. |
| 5,246,970 A | 9/1993 | Williamson et al. |
| 5,366,505 A | 11/1994 | Farber |
| 5,387,109 A | 2/1995 | Ishikawa et al. |
| 5,420,120 A | 5/1995 | Boltralik |
| 5,811,446 A | 9/1998 | Thomas |
| 5,824,049 A | 10/1998 | Ragheb et al. |
| 5,834,032 A * | 11/1998 | Song ................ 424/641 |
| 5,852,009 A | 12/1998 | Cerami et al. |
| 5,854,271 A | 12/1998 | Thomas et al. |
| 5,906,996 A | 5/1999 | Murphy |
| 5,972,985 A | 10/1999 | Thomas et al. |
| 5,980,914 A | 11/1999 | Gerolymatos |
| 6,147,070 A | 11/2000 | Facchini |
| 6,309,380 B1 | 10/2001 | Larson et al. |
| 6,329,414 B1 | 12/2001 | Thomas et al. |
| 6,348,465 B1 | 2/2002 | Baker |
| 6,576,672 B1 | 6/2003 | Murphy |
| 6,610,693 B2 | 8/2003 | Baker |
| 6,821,954 B2 | 11/2004 | Reid et al. |
| 6,855,511 B2 | 2/2005 | Baker |
| 6,884,575 B2 | 4/2005 | Cooper et al. |
| 6,897,243 B2 | 5/2005 | Baker et al. |
| 6,951,890 B2 | 10/2005 | Cooper et al. |
| 2002/0034775 A1 | 3/2002 | Baker |
| 2003/0013772 A1 | 1/2003 | Murphy et al. |
| 2003/0045506 A1 | 3/2003 | Baker |
| 2003/0055003 A1 | 3/2003 | Bar-Or et al. |
| 2003/0055113 A1 | 3/2003 | Wang et al. |
| 2003/0139312 A1 | 7/2003 | Caswell |
| 2003/0166561 A1 | 9/2003 | Cooper et al. |
| 2003/0186946 A1 | 10/2003 | Cooper et al. |
| 2003/0203973 A1 | 10/2003 | Cooper et al. |
| 2003/0232799 A1 | 12/2003 | Wang et al. |
| 2004/0019087 A1 | 1/2004 | Ternansky et al. |
| 2004/0023854 A1 | 2/2004 | Cooper et al. |
| 2004/0038861 A1 | 2/2004 | Cooper et al. |
| 2004/0076603 A1 | 4/2004 | Peled et al. |
| 2004/0142393 A1 | 7/2004 | Cooper et al. |

(Continued)

FOREIGN PATENT DOCUMENTS

| | | |
|---|---|---|
| DE | 3217071 A1 | 11/1983 |
| EP | 2192789 A | 1/1988 |
| EP | 2192790 A | 1/1988 |
| EP | 0331014 | 2/1989 |
| EP | 0426066 A2 | 5/1991 |

(Continued)

OTHER PUBLICATIONS

Medline Abstract No. 97217050, Kumar, Indian Journal of Experimental Biology, (May 1996) 34(5), 391-402.*
Medline Abstract No. 96432582, Oka et al., Japanese Journal of Pharmacology, (Jun. 1996) 71(2), 89-100.*
Medline Abstract No. 97074593, Smith et al., CA: A Cancer Journal for Clinicians, (Nov.-Dec. 1996), 46(6), 343-63.*

(Continued)

*Primary Examiner*—Raymond J Henley, III

(57) ABSTRACT

Novel methods of treating a patient for diseases, disorders, and conditions including diabetes mellitus, comprising administering, for example, copper binding compounds.

50 Claims, 5 Drawing Sheets

U.S. PATENT DOCUMENTS

| | | |
|---|---|---|
| 2004/0259945 A1 | 12/2004 | Brewer et al. |
| 2005/0002876 A1 | 1/2005 | Yukl et al. |
| 2005/0009760 A1 | 1/2005 | Wang et al. |
| 2005/0031651 A1 | 2/2005 | Gervais et al. |
| 2005/0047998 A1 | 3/2005 | Cooper et al. |
| 2005/0074756 A1 | 4/2005 | Cooper et al. |
| 2005/0085555 A1 | 4/2005 | Murphy et al. |
| 2005/0159364 A1 | 7/2005 | Cooper et al. |
| 2005/0159489 A1 | 7/2005 | Baker et al. |

FOREIGN PATENT DOCUMENTS

| | | |
|---|---|---|
| EP | 0 576 838 A2 | 1/1994 |
| EP | 1234585 | 8/2002 |
| JP | 7118148 | 5/1995 |
| JP | 2000204037 | 7/2000 |
| PL | 202419 | 12/1979 |
| WO | WO 8201804 A1 | 5/1982 |
| WO | WO 85/04169 A1 | 9/1985 |
| WO | WO 87-05505 A1 | 9/1987 |
| WO | WO 95/11690 A1 | 5/1995 |
| WO | WO 95/17900 A1 | 7/1995 |
| WO | WO 96/12483 A1 | 5/1996 |
| WO | WO 9840071 A1 | 9/1998 |
| WO | WO 99/39712 A1 | 8/1999 |
| WO | WO 9945907 A2 | 9/1999 |
| WO | WO 00/18392 A1 | 4/2000 |
| WO | WO 00/18891 A1 | 4/2000 |
| WO | WO0078805 A1 | 12/2000 |
| WO | 02/43722 | 6/2002 |
| WO | WO0279785 A2 | 10/2002 |
| WO | WO03045424 A1 | 6/2003 |
| WO | WO03062275 A1 | 7/2003 |
| WO | WO03063880 A1 | 8/2003 |
| WO | WO 03/075910 A1 | 9/2003 |
| WO | WO 03/077901 A1 | 9/2003 |
| WO | WO03074559 A1 | 9/2003 |
| WO | WO 03082259 A1 | 10/2003 |
| WO | WO03093311 A1 | 11/2003 |
| WO | 03/099223 | 12/2003 |
| WO | WO2004012760 A1 | 2/2004 |
| WO | WO2004012761 A1 | 2/2004 |
| WO | WO2004017956 A1 | 3/2004 |
| WO | WO2004017957 A1 | 3/2004 |
| WO | WO2004056861 A2 | 7/2004 |
| WO | WO2004065614 A2 | 8/2004 |
| WO | WO2004083215 A2 | 9/2004 |
| WO | WO2004087160 A1 | 10/2004 |
| WO | WO2005040205 A1 | 5/2005 |
| WO | WO2005058294 A1 | 6/2005 |

OTHER PUBLICATIONS

Medline Abstract No. 1998029329, Rickels et al., Journal of Clinical Psychiatry, (1997) 58 Suppl. 11, 4-10.*

Harrison's Principles of Internal Medicine, 13th Ed., vol. 1, published 1994 by McGraw-Hill, Inc. (NY), pp. 1108-1116.*

The Merck Manual of Diagnosis and Therapy, 14th Ed., published 1982 by Merck, Sharp & Dohme Research Laboratories (NJ), pp. 386-389 and 1036-1053.*

American Diabetes Association. (1997). "Report of the Expert Committee on the Diagnosis and Classification of Diabetes Mellitus", Diabetes Care 20:1183.

American Diabetes Association. (1998). "Economic Consequences of Diabetes Mellitus in the U.S. in 1997", Diabetes Care 21(2):296-309.

Anaja, (1997). "Diagnostic performance of red cell sorbitol assay in a Nigerian teaching hospital", Clinica Chimica Acta. 262:1.

Baker, et al. (1993). "Mechanism of fructosamine assay: evdence against role of superoxide as intermediate in nitroblue tetrazolium reduction". Clin Chem. 39(12):2460.

Barthelmebs, M. et al. (1990). "L-Dopa and Streptozotocin-Induced Diabetic Nephropathy in Rats", American Journal of Hypertension 3(6) Part 2:72S-74S.

Barthelmebs, M. et al. (1991). "Effects of Dopamine Pro-drugs and Fenoldopam on Glomerular Hyperfiltration in Streptozotocin-Induced Diabetes in Rats", Journal of Cardiovascular Pharmacology 18(2):243-253.

Barthlmebs, M. et al. (1995). "Pathophysiological Role of Dopamine in the Kidney: Effects in Diabetes Mellitus and after Contralateral Nephrectomey", Hypertens. Res. 18(Suppl. I):S131-S136.

Baynes, J. W. (1991). "Role of Oxidative Stress in Development of Complications in Diabetes", Diabetes 40:405-412.

Boiadzhieva, N. (1990) "The Effect of Dopaminergic Pharmocological Agents on the Pancreatic Islet Apparatus in Rats", Eksp Med Morfol 29(3):20-26. (English abstract).

Borgstrom, L. et al. (1986). "Pharmacokinetics of N-Acetylcysteine in Man", Eur J Clin Pharmacol 31:217-222.

Chan, P.C. and Bielski, B.H.J. (1974) "Enzyme-catalyzed Free Radical Reactions with nicotinamide Adenine Nucleotides", J Biol Chem 249(4):1317-1319.

Chan, P.C. and Bielski, B.H.J. (1980). "Glyceraldehyde-3-Phosphate Dehydrogenase-catalyzed Chain Oxidation of Reduced Nicotinamide Adenine Dinucleotide by Perhydroxyl Radicals", J Biol chem 255(3):874-876.

Chaturvedi, N. et al. (1998). "Effect of Lisinopril on Progression of Retinopathy in Normotensive People with Type 1 Diabetes", The Lancet 351:28-31.

Dahlman, et al., (2000). "Long-term treatment of Wilson's disease with triethylene tetramine dihydrochloride (trientine),", YJM 9=88(9):609-616.

Deckert T. et al. (1978). "Prognosis of Diabetics with Diabetes Onset before the Age of Thirtyone", Diabetologia 14:363-370.

Dubois, R.S. et al. (1970). "Triethylene Teramine Dihydrochloride in Wilson's Disease", Lancet 2(7676):775.

Duchin, K.L. et a. (1988). "Pharmacokinetics of Captopril in Healthy Subjects and in Patients with Cardiovascular Diseases", Clin Pharmacokinetics 14:241-259.

Elstner, E.f. and Heupel, A. (1976). "Inhibition of Nitrite Formation from Hydroxylammonium-chloride: A Simple Assay for Superoxide Dismutase", Anal Biochem 70:616-620.

Epstein, O. and Sherlock, S. (1980). "Triethylene Tetramine Dihydrochloride Toxicity in Primary Biliary Cirrhosis", Gastroenterology 78(6):1442-1445.

Chiara et al: "Novel Degradation Pathway of Glycated Amino Acids into Free Fructosamine by a Pseudomonas sp. Soil Strain Extract." Journal of Biological Chemistry, vol. 270, No. 1, 1995, pp. 218-224, XP002189588 ISSN: 218-224.

Greenman, D. et al. (1996). "Subchronic toxicity of triethylenetetramine dihydrochloride in B6C3F1 mice and F344 rats", Fundam. Appl. Toxicol. 29(2):185-193.

Greenstock, C.L. and Ruddock, G.W. (1976). "Determination of superoxide ($O_2$-) Radical Anion Reaction Rates Using Pulse Radiolysis", Int J Radiat Phys Chem 8:367-369.

Halliwell, B. (1976). "An Attempt to Demonstrate a Reaction between Superoxide and Hydrogen Peroxide", FEBS Lett 72(1):8-10.

Halliwell, B. and Gutteridge, J.M.C. (1989). "Free Radicals in Biology and Medicine", Clarendon Press, Oxford, pp. 136-176.

Haslam, R.H. et al. (1980). "Treatment of Wilson's Disease with Triethylene Tetramine Dihydrochloride," Dev Pharmacol Ther 1 (5):318-324.

Holdiness M.R. (1991). "Clinical Pharmacokinetics of N-Acetylcysteine", Clin Pharmacokinet 20(2):123-124.

Horiuchi, T. et al. (1989). "Purification and Properties of Fructosylamino Acid Oxidase from Corynebacterium sp. 2-4-1," Agric Biol Chem 53(1):103-110.

Ido, Y. et al. (1996). "Interactions between the Sorbitol Pathway, Non-enzymatic Glycation, and Diabetic Vascular Dysfunction," Nephrol Dial Transplant 11 [Suppl 5]:72-75.

Karlsson, K. and Marklund, S. L. (1987). "Heparin-induced Release of Extracellular Superoxide Dismutase to Human Blood Plasma," Biochem J 242:55-59.

Kashihara, N. et al. (1992). "Selective Decreased de novo Synthesis of Glomerular Proteoglycans under the Influence of Reactive Oxygen Species," Proc Natl Acad Sci USA 89:6309-6313.

Klein, R. et al. (1985). "Retinopathy in Young-onset Diabetic Patients," Diabetes Care 8(4):311-315.

Kodama, H. et al. (1997). "Metabolism of Administered Triethylene Tetramine Dihydrochloride in Humans," Life Sci 61(9)899-907.

Marklund, S. L. et al. (1982). "Superoxide Dismutase in Extracellular Fluids," Clin Chimica Acta 126:41-51.

Mattock, M. B. et al. (1998). "Microalbuminuria and Coronary Heart Disease in NIDDM: An Incidence Study," Diabetes 47:1786-1792.

McCord, J. M. and Fridovich, I. (1969). "Superoxide Dismutase: An Enzymic Function for Erythrocuprein (Hemocuprein)," J Biol Chem 244(22):6049-6055.

Misra, H. P. and Fridovich, I. (1972). "The Role of Superoxide Anion in the Autoxidation of Epinephrine and a Simple Assay for Superoxide Dismutae," J Biol Chem 247(10):3170-3175.

Misra, H. P. and Fridovich, I. (1977). "Superoxide Dismutase: 'Positive' Spectrophotometric Assays," Anal Biochem 79:553-560.

Mizobuchi, N. et al. (1993). "Serum Superoxide Dismutase (SOD) Activity in Diabetes Mellitus," Rinsho Byori 41:673-678. (English Abstract).

Mogensen, C. E. and Christensen, C. K. (1984). "Predicting Diabetic Nephropathy in Insulin-dependent Patients," New Eng J Med 311(2):89-93.

Mogensen, C. E. et al. (1992). "Microalbuminuria in Non-insulin-dependent Diabetes," Clin Nephrol 38 (suppl 1):S28-S38.

Morita J. et al. (1992). "Wilson's disease treatment by triethylene tetramine dihydrochloride (trientine, 2HC10: long-term observations", Dev. Pharmcacol. Ther. 19(1):6-9.

Morpurgo, L. et al. (1990). "The Role of Copper in Bovine Serum Amine Oxidase," Biol Metals 3:114-117.

Muchova, J., et al. (1999). "Antioxidant systems inpolymorphonuclear leucocytes of type 2 diebetes mellitus", Diabet Med. 16(1):74-78.

Muruganandam A. et al. (1994). "ELISA for In Vivo Assessment of Nonenzymatically Flycated Platelet Glutathione Peroxidase", Clin. Biochem. 27(4):293-298.

Obach, R. et al. (1984). "The Pharmacokinetic Profile of Carbidopa in Dogs," J Pharm Pharmacol 36:415-416.

Palcic, M. M. and Janes, S. M. (1995). "Spectrophotometric Detection of Topa Quinone," Meth Enzymol 258:34-38.

Pappert, E. J. et al. (1997). "The Stability of Carbidopa in Solution," Movement Disorders 12(4):608-623.

Picard, S. et al. (1996). "Minimally Oxidised LDL as Estimated by a New Method Increase in Plasma of Type 2 Diabetic Patients with Atherosclerosis of Nephropathy," Diabetes and Metabolism 22(1):25-30.

Robbins, S. L. et al. (1984). "Pathologic Basis of Disease," 3.sup.rd ed., W. B. Saunders Company: Philadelphia, pp. 991-1061.

Saeki, H. et al. (1998). "Malignant Syndrome Associated with Disseminated Intravascular Coagulation and a High Level of Amylase in Serum, Followed by Diabetic Coma in an Elderly Patient with Parkinson's Disease during L-Dopa Therapy," Nippon Ronen Igakkai Zasshi 35(2):139-144. (English abstract).

Saxena, A. K. et al. (1996). "Purification and Characterization of a Membrane-bound Deglycating Enzyme (1-Deoxyfructosyl Alkyl Amino Acid Oxidase, EC 1.5.3) from a *Pseudomonas* sp. Soil Strain," J Biol Chem 271(51):32803-32809.

Siegemund R. et al. "Mode of action of triethylenetetramine dihydrochloride on copper metabolism in Wilson's disease", Acta. Neurol. Scand. 83(6):364-366, date unavailable.

Skrha, J. et al. (1996). "Relationship of Oxidative Stress and Fibrinolysis in Diabetes Mellitus", Diabet. Med. 13(9):800-805.

Smith, P. R. and Thornalley, P. J. (1992). "Mechanism of the Degradation of Non-Enzymatically Glycated Proteins under Physiological Conditions," Eur. J. Biochem. 210:729-739.

Smith, S. A. and Pogson, C. I. (1977). "Trytophan and the Control of Plasma Glucose Concentrations in the Rat," Biochem J 168(3):495-506.

Somani, B., et al. (1999). "Elimination of superoxide dismutase interference in fructosamine assay", Clin. Biochem. 32(3):185-188.

Sone, H. et al. (1996). "Inhibition of Hereditary Hepatitis and Liver Tumor Development in Lung-Evans Cinnamon Rats by the Copper-Chelating Agent Trientine Dihydrochloride," Hepatology 23 (4):764-770.

Sugimoto, H. et al. (1999). "Advanced glycation end products-cytokine-nitric oxide sequence pathway in the development of diabetic nephraphathy: aminoguanidine ameliorates the overexpression of tumour necrosis factor-alpha and inducible nitric oxide synthase in diabetic rat glomeruli", diabetologia 42(7):878-886.

Talseth, T. (1976). "Studies on Hydralazine," European Journal of Clinical Pharmacology 10(6):395-401.

Talseth, T. (1977). "Kinetics of Hydralazine Elimination," Clinical Pharmacology Therapeutics 21(6):715-720.

Tanabe, R. et al. (1996). "Uptake Mechanism of Trientine by Rat Intestinal Brush-border Membrane Vesicles," J Pharm Pharmacol 48:517-521.

The Diabetes Control and Complications Trial Research Group. (1993). "The Effect of Intensive Treatment of Diabetes on the Development and Progression of Long-term Complications in Insulin-dependent Diabetes Mellitus," N Eng J Med. 329(14):977-986.

UKPDS Study Organisation. (1998). "Intensive Blood-glucose Control with Sulphonylureas or Insulin Compared with Conventional Treatment and Risk of Complications in Patients with Type 2 Diabetes (UKPDS 33)," Lancet 352:837-853.

Vailly, B. et al. (1990). "Prevention of L-dopa of Early Renal Consequences of Diabetes Induced by Stepotozocin in Rats," Arch Mal Coeur Vaiss 83(8):1259-1262. (English abstract).

Walshe, J. M. (1973). "Copper Chelation in Patients with Wilson's Disease: A Comparison of Penicillamine and Triethylene Tetramine Dihydrochloride," Q J Med New Series, XLII(167):441-452.

Walshe, J. M. (1982) "Treatment of Wilson's Disease with Trientine (Triethylene Tetramine) Dihydrochloride," Lancet 8273:643-647.

Witztum, J. L. (1993). "Role of Oxidised Low Density Lipoprotein in Atherogenesis," Br Heart J 69 (Suppl):S12-S18.

Wolff, S. P. et al. (1991). "Protein Glycation and Oxidative Stress in Diabetes Mellitus and Ageing," Free Rad Biol Med 10:339-352.

Wynn, J. E. et al. (1970). "The Toxicity and Pharmacodynamics of EGTA: Oral Administration to Rats and Comparisons with EDTA," Toxicol Appl Pharmacol 16:807-817.

Yanagisawa, T. et al. "Subacute and chronic toxicity studies of triethylenetetramine dihydrochloride (TJA-250) by oral administration to F-344 rats", J. Toxicol. Sci. 23 Suppl. 4:619-642, date unavailable.

Yucel, D. et al. (1998). "Increased Oxidative Stress in Dilated Cardiomyopathic Heart Failure," Clin Chem 44(1)148-154.

Armbruster D A: "Fructosamine Structure Analysis and Clinical Usefulness" Clinical Chemistry, vol. 33, No. 12, 1987, pp. 2153-2163, XP001061531 ISSN: 0009-9147.

Gillery P et al.: "Glycation of proteins as a source of superoxides" Diabete Metab, vol. 14, No. 1, 1988, pp. 25-30, XP001058074.

Green T and Shangguan X: "Stoichoimetry of O2 Metabolism and NADPH Oxidation of the Cell-free Latent Oxidase Reconstituted from Cytosol and Solubilized Membrane from Resting Human Neutrophils" J. Biol. Chem., vol. 268, No. 2, Jan. 15, 1993, pp. 857-861, XP002192176.

Laight DW et al.: "Microassay of superoxide anion scavenging activity in vitro" Environmental Toxicology and Pharmacology, vol. 3, 1997, pp. 65-68, XP002192177.

Takahashi Motoko et al: "Isolation, purification, and characterization of amadoriase isoenzymes (fructosyl amine-oxygen oxidoreductase EC 1.5.3) from *Aspergillus* sp." Journal of Biological Chemistry, vol. 272, No. 6, 1997, pp. 3437-3443, XP002189585 ISSN: 0021-9258.

Takahashi Motoko et al: "Molecular cloning and expression of amadoriase isoenzyme (fructosyl amine:oxygen oxidoreductase, EC 1.5.3) from *Aspergillus fumigatus*." Journal of Biological Chemistry, vol. 272, No. 19, 1997, pp. 12505-12507, XP002189584 ISSN: 0021-9258.

Yoshida Nobuyuki et al: "Distribution and properties of fructosyl amino acid oxidase in fungi." Applied and Environmental Microbiology, vol. 61, No. 12, 1995, pp. 4487-4489, XP000561863 ISSN: 0099-2240.

Allen, K.G D. et al. (Jan. 1987). "Tetramine Cupruretic Agents: a Comparison in Dogs", Am. J. Vet. Res. 48(1):28-30.

Borthwick, T.R. et al. (Apr. 1980). "Copper Chelating Agents: A Comparison of Cupruretic Responses to Various Tetramines and D-Penicillamine", J. Lab. Clin. Med. 95(4):575-580.

Cameron, N.E. and Cotter, M.A. (Aug. 1995). "Neurovascular Dysfunction in Diabetic Rats. Potential Contribution of Autoxidation and Free Radicals Examined Using Transition Metal Chelating Agents", J. Clin. Invest. 96(2): 1159-1163.

Cameron, N.E. et al. (1995). "Ciliary Neurontrophic Factor Improves Nerve Conduction and Regeneration in Experimental Diabetes," Diabetologia 38(Suppl. I):A233 Abstract.

Cohen, N. L. et al. (1983). "The Effect of Copper Chelating Drugs on Liver Iron Mobilization in the Adult Rat," Biochemical and Biophysical Research Communications 113(1):127-134.

Dwivedi, R. S. et al. (1978). "The Effect of Triethylene Tetramine Upon the Selective Removal of Nickel (II), Iron (II), Manganese (II) and Tin (II) in Rats," Chemosphere 11:925-932.

Iseki, K. et al. (1992). "Comparison of Disposition Behavior and De-Coppering Effect of Triethylenetetramine in Animal Model for Wilson'S Disease (Long-Evans Cinnamon Rat) with Normal Wistar Rat," Biopharmaceutics & Drug Disposition 13:273-283.

Keegan, A. et al. (1996). "Transition Metal Chelators and Anti-Oxidants Prevent the Development of Defective Endothelium-Dependent Relaxation in Aortas from Diabetic Rats," Diabetic Medicine 13(Suppl. 1):S17 Abstract.

Keegan, A. et al. (Sep. 27, 1999). "Effects of Chelator Treatment on Aorta and Corpus Cavernosum From Diabetic Rats," Free Radical Biology & Medicine 27 (5-6):536-543.

Kodama, H. et al, (1997). "Metabolism of Administered Triethylene Tetramine Dihydrochloride in Humans," Life Sciences 61(9):899-907.

Love, A. et al. (Oct. 24, 1996). "Nerve Function and Regeneration in Diabetic and Galactosaemic Rats: Antioxidant and Metal Chelator Effects," European Journal of Pharmacology 314:33-39.

McQuaid, A. And Mason, J. (1990). "A Comparison of the Effects of Penicillamine, Trientine, and Trithiomolybdate on [.sup.35 S]-labeled Metallothionein In Vitro; Implications for Wilson's Disease Therapy," Journal of Inorganic Biochemistry 41, 87-92.

Pieper, G. M. et al. (1993). "Hydroxyl Radicals Mediate Injury to Endothelium-Dependent Relaxation in Diabetic Rat," Molecular and Cellular Biochemistry 122:139-145.

Planas-Bohne, F. (1979). "Influence of Several Chelating Agents on the Excretion and Organ Concentration of Copper in the Rat," Toxicology and Applied Pharmacology 50:337-345.

Shimizu, N. et al. (1997). "Age-Related Copper, Zinc, and Iron Metabolism in Long-Evans Cinnamon Rats and Copper-Eliminating Effects of S-Penicillamine and Trienthine-2HC1," The Journal of Trace Elements in Experimental Medicine 10:49-59.

Sone, H. et al. (Apr. 1996). "Inhibition of Hereditary Hepatitis and Liver Tumor Development in Long-Evans Cinnamon Rats by the Copper-Chelating Agent Trientine Dihydrochloride," Hepatology 23(4):764-770.

Tandon, S. K. et al. (1984). "Effect of Metal Chelators Agent, Trientine, Suppresses Tumor Development and Angiogenesis in the Murine Hepatocellular Carcinoma Cells," Int. J. Cancer 94:768-773.

Appelbaum et al., "The Protective Role of Neocuproine Against Cardiac Damage in Isolated Perfused Rat Hearts", Free Radical Biology & Medicine, vol. 8, pp. 133-143, 1990; Pergamon Press USA.

Beshgetoor et al., "Clinical conditions altering cooper metabolism in humans", Am J Clin Nutr 1998; 67 (suppl):1017S-21S.

Bingham et al., "Characterization of intracellular copper pools in rat hepatocytes using the chelator diamsar", Am. J. Physiol. 272 (Gastrointest. Liver Physiol. 35): G1400-G1407, 1997.

Brownlee et al., "Aminoguanidine Prevents Diabetes-Induced Arterial Wall Protein Cross-Linking", Science, New Series, vol. 232, No. 4758 (Jun. 27, 1986), 1629-1632.

Bryszewska et al., "Oxidative Processes in Red Blood Cells from Normal and Diabetic Individuals", Biochemistry and Molecular Biology International, vol. 37, No. 2, 345-354, Oct. 1995.

Chang et al., "Increased Collagen Cross-Linkages in Experimental Diabetes Reversal by β-Aminopropionitrile and D-Penicillamine", Diabetes, vol. 29, Oct. 1980, 778-781.

Cooper, "The Action of Mebanazine, a Mono Amine Oxidase Inhibitor Antidepressant Drug in Diabetes", Int. J. Neurophyschiatry, 4:342-5(1966).

Ekblom, "Potential Therapeutic Value of Drugs Inhibiting Semicarbazide-Sensitive Amine Oxidase: Vascular Cytoprotection in Diabetes Mellitus", Pharmacological Research, vol. 37, No. 2, 1998.

Elling, "Penicillamine, Captopril, and Hypoglycemia", Annals of Internal Medicine, vol. 103, No. 4, Oct. 1985.

Hoffken et al., "Excretion of Zinc in Diabetics Receiving Penicillamine", Z Klin Chem Klin Biochem. Jan. 7, 1969; (1):4-7.

Leinonen et al., "Susceptibility of LDL to oxidation is not associated with the presence of coronary heart disease or renal dysfunction in NIDDM patients", Clinica Chimica Acta 275 (1998) 163-174.

McArdle et al., "Effect of chelators on copper metabolism and copper pools in mouse hepatocytes," Am. J. Physiol. 256 (Gastrointest. Liver Physiol. 19): G667-G672, 1989.

Norton et al., "Amioguanidine Prevents the Decreased Myocardial Compliance Produced by Streptozotocin-Induced Diabetes Mellitus in Rats", Circulation. 1996;93:1905-1912.

Ou et al., Thioctic (Lipoic) Acid: A Therapeutic Metal-Chelating Antioxidant?, Biochemical Pharmacology, vol. 50, No. 1, pp. 123-126. (1995).

Pucheu, et al., "Effect of Iron Overload in the Isolated Ischemic and Reperfused Rat Heart,", Cardiovascular Drugs and Therapy, 1993; 7:701-711.

Rogers et al., "Hydrazine Stress in the Diabetic: Omithine Decarboxylase Activity", Biochemical Medicine and Metabolic Biology, 40, 46-49 (1988).

Salonen et al., Serum Copper and the Risk of Acute Myocardial Infarction: A Prospective Population Study in Men in Eastern Finland, Am. J. Epidemiol, 1991; 134: 268-76.

Saunders, "The Effects of Excess Renal Copper on Kidney Function in the Diabetic Rat", Research Communications in Chemical Pathology and Pharmacology, vol. 52, No. 1, Apr. 1986, 45-49.

Sugimoto et al., "Effects of Aminoguanidine on Structural Alterations of Microvessels in Peripheral Nerve of Streptozotocin Diabetic Rats", Microvascular Research 53, 105-112 (1997).

Tessier et al., "Effect of pH, phosphate and copper on the interaction of glucose with albumin", Glycoconjugate Journal 15, 571-574 (1998), U.K.

Vesely et al., "New Strategies in the Prevention and Management of Diabetes and Its Complications," Online Journal, Jacksonville Medicine: May 1997. http://www.onlinejournal.com.

Walter et al, "Copper, Zinc, Manganese, and Magnesium Status and Complications of Diabetes Mellitus", Diabetes Care, vol. 14, No. 11, Nov. 1991.

Wolff et al., "Aminoguanidine Is an Isoform-Selective, Mechanism-Based Inactivator of Nitric Oxide Synthase", Archives of Biochemistry and Biophysics, vol. 316, No. 1, Jan. 10, pp. 290-301, 1995.

Wolff et al., "Inactivation of Nitric Oxide Synthase by Substituted Aminoguanidines and Aminoisothioureas[1] ", JPET 283:265-273, 1997.

Wolff, "Diabetes Mellitus and Free Radicals", The British Council (1993), vol. 49, No. 3 pp. 642-652.

Yagihashi et al., "Effect of Aminoguanidine on Functional and Structural Abnormalities in peripheral Nerve of STZ-Induced Diabetic Rats", Diabetes, vol. 41, Jan. 1992, 47-52.

Young et al., "The Effects of Desferrioxamine and Ascorbate on Oxidative Stress in the Streptozotocin Diabetic Rat", Free Radical Biology & Medicine, vol. 18, No. 5, pp. 833-840, 1995.

Yu et al., "Aminoguanidine inhibits semicarbazide-sensitive amine oxidase activity: implications for advanced glycation and diabetic complications", Diabetologia (1997) 40: 1243-1250.

Yoshii, J. et al. (2001). "The Copper-Chelating Agent, Trientine, Suppresses Tumor Development and Angiogenesis in the Murine Hepatocellular Carcinoma Cells," Int. J. Cancer 94:768-773.

Gerhardinger, C. et al. (1995). "Novel Degradation Pathway of Glycated Amino Acids into Free Fructosamine by a Pseudomonas sp. Soil Strain Extract," J Biol Chem 270(1):218-224.

Encyclopedia of Toxicology, vol. 1, Philip Wexler, ed. published 1998 by Academic Press (San Diego) pp. 376-378.

Pasterkamp & Falk, "Atherosclerotic Plaque Rupture: an Overview," J. Clin. Basic Cardiol. 3:81-86 (2000).

Baynes, "Role of Oxidative Stress in Development of Complications in Diabetes", *Diabetes*, vol. 40, Apr. 1991.

Berenshtein et al., "Roles of Ferritin and Iron in Ischemic Preconditioning of the Heart", *Molecular and Cellular Biochemistry*, 234/235: 283-292, 2002; Kluwer Academic Publishers, Netherlands.

Duffy et al., "Iron Chelation Improves Endothelial Function in Patients with Coronary Artery Disease", *Circulation*. 2001; 103:2799-28204.

Howes et al., "Role of Stored Iron in Atherosclerosis", *Journal of Vascular Nursing*, vol. XVIII, No. 4, 109-114, no date available.

Hunt et al., "Ascorbic Acid Oxidation: a Potential Cause of the Elevated Severity of Atherosclerosis in Dibetes Mellitus?", FEBS 11659, vol. 311, No. 2, 161-164, no date available.

Walshe, "Triethylene Tetramine Dihydrochloride in Wilson's Disease", *Lancet*, 1969, ii, 1401.

Cherny R.A. et al: 'Chelation and Interaction: Complementary Properties in a Compound for the Treatment of Alzheimer's Disease' J Struct Biol. vol. 130, No. 23, Jun. 2000, pp. 209-216.

Norga K. et al: 'Prevention of Acute Autoimmune Encephalomyelitis and Abrogation of Relapses in Murine Models of Multiple Sclerosis by the Proteate inhibitor D-Penicillamine' Inflamm Res. vol. 44, No. 12, Dec. 1995, pp. 529-534.

Brem S.: 'Angiogenesis and Cancer Control: From Concept to Therapeutic Trial' Cancer Control vol. 6, No. 5, Oct. 1999, pp. 436-458.

Rossi L. et al: 'Increase Susceptibility of Copper- Deficient Neuroblastoma Cells to Oxidative Stress-Mediated Apoptosis' Free Radic Biol Med. vol. 30, No. 10, May 15, 2001, pp. 1177-1187.

Chemistry Abstracts Registry No. 4429-04-3, 57-48-7, 1 854-25-7, date unavailable.

Konarkowska B, Aitken JF, Kistler J, Zhang S, Cooper GJ., Thiol reducing compounds prevent human amylin-evoked cytotoxicity, FEBS J. Oct. 2005;272(19):4949-59.

Cooper GJ, et al., Demonstration of a hyperglycemia-driven pathogenic abnormality of copper homeostasis in diabetes and its reversibility by selective chelation: quantitative comparisons between the biology of copper and eight other nutritionally essential elements in normal and diabetic individuals, Diabetes. May 2005;54(5):1468-76.

Xu A et al., Testosterone selectively reduces the high molecular weight form of adiponectin by inhibiting its secretion from adipocytes, J Biol Chem. May 6, 2005;280(18):18073-80. Epub May 6, 2005.

Wang Y et al., Adiponectin inhibits cell proliferation by interacting with several growth factors in an oligomerization-dependent manner, J Biol Chem. May 6, 2005;280(18):18341-7. Epub Feb. 25, 2005.

Wang Y et al., Proteomic and functional characterization of endogenous adiponectin purified from fetal bovine serum, Proteomics. Dec. 2004;4(12):3933-42.

Cooper GJ et al., Regeneration of the heart in diabetes by selective copper chelation, Diabetes. Sep. 2004;53(9):2501-8.

Xu A et al, Chronic treatment with growth hormone stimulates adiponectin gene expression in 3T3-L1 adipocytes, FEBS Lett. Aug. 13, 2004;572(1-3):129-34.

Xu A. et al., The fat-derived hormone adiponectin alleviates alcoholic and nonalcoholic fatty liver disease in mice, J Clin Invest. Jul. 2003;112(1):91-100.

Aitken JF et al., Suppression by polycyclic compounds of the conversion of human amylin into insoluble amyloid, Biochem J. Sep. 15, 2003;374(Pt 3):779-84.

Xu A et al, Identification of novel putative membrane proteins selectively expressed during adipose conversion of 3T3-L1 cells, Biochem Biophys Res Commun. May 17, 2002;293(4):1161-7.

Wang Y et al., Hydroxylation and glycosylation of the four conserved lysine residues in the collagenous domain of adiponectin. Potential role in the modulation of its insulin-sensitizing activity, J Biol Chem. May 31, 2002;277(22):19521-9. Epub Mar. 23, 2002.

Buchanan CM et al., Preptin derived from proinsulin-like growth factor II (proIGF-II) is secreted from pancreatic islet beta-cells and enhances insulin secretion, Biochem J. Dec. 1, 2001;360(Pt 2):431-9.

Cornish J et al., Effects of calcitonin, amylin, and calcitonin gene-related peptide on osteoclast development, Bone. Aug. 2001;29(2):162-8.

Wang Y et al., Alteration in phosphorylation of P20 is associated with insulin resistance, Diabetes. Aug. 2001;50(8):1821-7.

Wang Y et al., Phosphorylation of P20 is associated with the actions of insulin in rat skeletal and smooth muscle, Biochem J. Dec. 15, 1999;344 Pt 3:971-6.

Wang Y et al., Insulin and insulin antagonists evoke phosphorylation of P20 at serine 157 and serine 16 respectively in rat skeletal muscle, FEBS Lett. Nov. 26, 1999;462(1-2):25-30.

Wang Y et al., Amylin evokes phosphorylation of P20 in rat skeletal muscle, FEBS Lett. Aug. 20, 1999;457(1):149-52.

Cooper GJ et al., Amylin, amyloid and age-related disease, Drugs Aging. Sep. 1996;9(3):202-12.

Cooper GJ, Amylin and insulin co-replacement therapy for insulin-dependent (type 1) diabetes mellitus, Med Hypotheses. Nov. 1991;36(3):284-8.

Leighton B et al., Pancreatic amylin and calcitonin gene-related peptide cause resistance to insulin in skeletal muscle in vitro, Nature. Oct. 13, 1988;335(6191):632-5.

Witek E., et al., "Polycondensation of polyethylenepolyamines with aliphatic dicarboxylic acids", Polymers-Large Molecule Materials, The Institute of Polymers, The Lodz Polytechnic, 1976.

R. A. Cherny et al., "Chelation and Intercalation: Complementary Properties in a Compound for the Treatment of Alzheimer's Disease", Journal of Structural Biology, 130, 209-216 (2000).

S.C. Cunnane et al., "Copper Inhibits Pressor Responses to Noradrenaline but not Potassium. Interactions with Prostaglandins $E_1$, $E_2$, and $I_2$ and Penicillamine", Can. J. Physiol. Pharmacol. vol. 57, 35-40 (1979).

Leslie M. Klevay, "Coronary Heart Disease: the Zinc/ Copper Hypothesis[1,2]", The American Journal of Clinical Nutrition 28: 764-774 (1975).

P. Ou et al., "Activation of Aldose Reductase in Rat Lens and Metal-Ion Chelation by Aldose Reductase Inhibitors and Lipoic Acid", Free Rad. Res., vol. 25, No. 4, 337-346, (1996).

Vincent M. Monnier, "Transition Metals Redox: Reviving an Old Plot for Diabetic Vascular Disease", The Journal of Clinical Investigation, vol. 107, No. 7, 799-801 (2001).

S. M. Karmazyn et al., "Prostaglandin Concentrations Cause Cardiac Rhythm Disturbances. Effect Reversed by Low Levels of Copper or Chloroquine", Prostaglandins, vol. 15, (1978).

A. Nitenberg et al., "Coronary Artery Response to Physiological Stimuli Are Improved by Deferoxamine but not by L-Arginine in Non-Insulin-Dependent Diabetic Patients With Angiographically Normal Coronary Arteries and No Other Risk Factors", American Heart Association, (1997), XP-002366411.

S. P. Wolff, "Diabetes Mellitus and Free Radicals", British Medical Bulletin, vol. 49, No. 3, 642-652, (1993).

J. Y. Jeremy et al., "Copper Chelators Inhibit Platelet Thromboxane A2 Synthesis and Lipoxygenase Activity, In Vitro", J. Drug Dev Clin Pract 7, 119-126 (1995).

N. E. Cameron et al., "Neurvascular Dysfunction in Diabetic Rats", J. Clin. Invest., vol. 96, 1159-1163, (1995).

N. Shimizu et al., "Treatment and Management of Wilson's Disease", Pediatrics International 41, 419-422, (1999).

D. L. Eizirik et al., "1, 10 Phenanthroloine, a Metal Chelator, Protects Against Alloxan- but not Streptozotocin-Induced Diabetes", Journal of Free Radicals in Biology & Medicine, vol. 2, 189-192 (1986).

Z.Y. Jiang et al., "Spirohydantoin Inhibitors of Aldose Reductase Inhibit Iron-and Copper-Catalysed Ascorbate Oxidation in Vitro", Biochemical Pharmacology, vol. 42., No. 6, 1273-1278 (1991).

Y. Toshihiko et al., "Subacute and Chronic Toxicity Studies of Triethylenetetramine Dihydrochloride (TJA-250) by Oral Administration to F-344 Rats" Journal of Toxicological Sciences, vol. 23, No. 4, 619-642 (1998) Abstract (EP-002356395).

M. L. Failla et al., "Hepatic and Renal Metabolism of Copper and Zinc in the Diabetic Rat", American Journal of Physiology, vol. 244, No. 2, E115-E121 (1983) Abstract (XP-002366428).

M. L. Failla et al., "Altered Tissue Content and Cytosol Distribution of Trace Metals in Experimental Diabetes", Journal of Nutrition, vol. 111, No. 11, 1900-1909 (1981) Abstract (XP-002366429).

P. Ou et al., "Erythrocyte Catalase Inactivation (H-20-2 production) by Ascorbic Acid and Glucose in the Presence of Aminotriazole: Role of Transition Metals and Relevance to Diabetes", Biochemical Journal, vol. 303, No. 3, 935-940 (1994) Abstract (XP-002366430).

International Search Report from European Application EP99946470, date unavailable.

International Search Report from European Application EP03792902, date unavailable.

International Search Report from PCT/NZ2004/000325, date unavailable.

International Search Report from PCT/NZ2005/000337, date unavailable.

International Search Report from EP99946470, date unavailable.

* cited by examiner

TREATMENT OF DIABETES WITH COPPER BINDING COMPOUNDS

RELATED APPLICATIONS

This application is a continuation application of U.S. Ser. No. 10/226,685, filed Aug. 23, 2002 (now U.S. Pat. No. 6,897,243), which is a continuation of U.S. Ser. No. 09/975,751, filed Oct. 10, 2001 (now U.S. Pat. No. 6,610,693), which is a continuation application of U.S. Ser. No. 09/671,967, filed Sep. 27, 2000 (now U.S. Pat. No. 6,348,465), which is a National Stage application of international application PCT/NZ99/00161 (now published as WO/00/18392), filed Sep. 24, 1999, which claims the benefit of priority to New Zealand application 337042, filed Aug. 9, 1999; New Zealand application 334471, filed Mar. 3, 1999; New Zealand application 332079, filed Sep. 28, 1998; and New Zealand application 332084, filed Sep. 25, 1998; all documents listed herein are hereby incorporated by reference in their entirety.

FIELD

The present invention is in the field of biochemistry. More specifically, the invention involves fructosamine oxidase enzyme inhibitors. Methods of treatment, pharmaceutical compositions, dosage forms, uses of fructosamine oxidase enzyme inhibitors in medicine or for manufacturing pharmaceutical compositions, treatment regimes, and related combinations, methods and products are disclosed herein.

BACKGROUND

Diabetes mellitus is a common disorder affecting nearly 16 million Americans. See, for example, Report of the Expert Committee on the Diagnosis and Classification of Diabetes Mellitus. *Diabetes Care,* 20; 1183-97 (1997). Diabetic individuals are prone to complications which are a major threat to both the quality and the quantity of life. Almost half those diagnosed with diabetes before the age of 31 years die before they reach 50 years largely as a result of cardiovascular or renal complications, often with many years of crippling and debilitating disease beforehand. See, Deckert T., Poulsen J., Larsen M. *Diabetologia* 14: 363-70 (1978). It is estimated that diabetic individuals have a 25-fold increase in the risk of blindness, a 20-fold increase in the risk of renal failure, a 20-fold increase in the risk of amputation as a result of gangrene, and a 2- to 6-fold increased risk of coronary heart disease and ischemic brain damage. See, Klein R., Klein B., Moss S., Davis M., DeMets D. *Diabetes Care* 8; 311-5 (1985).

Largely because of these long-term complications, the cost of diabetes in the US was estimated as $98 billion in 1997 comprising $44 billion for direct medical costs such as inpatient and outpatient care plus $54 billion for indirect costs such as lost earnings and productivity, and premature death. Medical innovations that can slow the progression of diabetes have tremendous potential to mitigate the associated clinical and cost repercussions. See, American Diabetes Association, "Economic consequences of diabetes in the US in 1997," *Diabetes Care* 21: 296-309 (1998).

Elevated blood glucose levels are now regarded as causative of diabetic complications based on results of the Diabetes Complications and Control Trial (DCCT) and the United Kingdom Prospective Diabetes Study (UKPDS). See, N Eng J. Med. 379: 977-85 (1993) and Lancet 352: 837-53 (1998). The DCCT and the UKPDS have both demonstrated that the development of complications of diabetes is related with the degree of hyperglycemia and that the long-term outcome may be ameliorated by rigorous treatment. For example, prognosis is dramatically improved if capillary blood and glycated hemoglobin levels are maintained less than 150 mg/dL and 7.0% respectively.

The mechanism of glucose toxicity in the tissues of patients with diabetes mellitus is unknown. Glucose condenses with free amino groups on structural and functional proteins to form Schiff bases which, in turn, undergo a series of transformations to yield dark-brown Maillard products. It has been proposed that diabetes complications are caused by the non-enzymatic cross-linking of proteins. See, for example, Cerami A., Ulrich P. C., Brownlee M., U.S. Pat. No. 4,758,583 (1988). However, although increased protein cross-linking is seen in the tissues of people with long-standing diabetes, the role of Maillard products as a causative factor is certainly not clear. See, for example, Wolff S. P., Jiang Z. Y., Hunt J. V. Free Rad Biol Med 10; 339-52 (1991).

Amadori-rearrangement is the most important Maillard transformation because its product, fructosamine, is the precursor of all the browning products. A novel extracellular enzyme which catalyzes the elimination of fructosamines from glycated protein has been isolated. Enzymes which are related have been disclosed. See, for example, Gerhardinger C., et al. *J Biol Chem* 270 (1): 218-24 (1995); Saxena, A. K. et al., *J Biol Chem* 271 (51): 32803-9 (1996); and Horiuchi T, et al., *Agric. Biol. Chem.* 53 (1): 103-110 (1989). Based on its high specificity for glycated protein substrates and its use of oxygen as an acceptor, the enzyme may be classified as fructosamine oxidase 1.5.3. See, Enzyme Nomenclature, Recommendations of the Nomenclature Committee of the International Union of Biochemistry, Academic Press, London pp. 19-22, (1979).

Fructosamine oxidase is a copper metalloenzyme which belongs to the copper amine oxidase group of enzymes which have previously been isolated from bacteria, fungi, yeast, and mammalian sera. Products of the fructosamine oxidase catalyzed reaction are free unglycated protein, α-dicarbonyl sugar, and the active oxygen species superoxide. A highly specific copper chelator, triethylenetetramine dihydrochloride, is an irreversible inhibitor of fructosamine oxidase activity. See, for example, Morpurgo L, et al. Biol Met 3: 114-7 (1990).

Increased fructosamine oxidase activity may cause many of the recognized sequelae of diabetes by degrading fructosamines bound to basement membrane proteins and generating reactive oxygen species as reaction products. For example, superoxide anions cause an increase in intracellular calcium which modulates the activity of nitric oxide synthase. Nitric oxide is a potent vasodilator and it has been implicated in the vascular dysfunction of early diabetes. See, for example, Ido Y., Kilo C., Williamson J. R. *Nephrol Dial Transplant* 11 Suppl 5: 72-5 (1996). Reactive oxygen species also cause a drastic dose-dependent decrease in de novo synthesis of heparin sulfate proteoglycans leading to a reduction in anionic sites on the glomerular basement membrane and an increase in basement membrane permeability to cationic plasma proteins such as albumin. See, Kashira N., Watanabe Y., Malin H., Wallner E. I., and Kanwar Y. S. *Proc Natl Acad Sci USA* 89: 6309-13 (1992). Increased urinary albumin clearance is a risk indicator in people with diabetes mellitus both for evolving renal disease and for early mortality mainly from coronary heart disease. See, for example, Mattock M. B., Barnes D. J., Viberti G. C., et al. *Diabetes* 47: 1786-92 (1998).

Once natural anti-oxidant defenses are exceeded, hydroxyl radicals may be generated from superoxide via a copper catalyzed Haber-Weiss reaction. See, Halliwell B. and Gutteridge J. M. C. "Free radicals in Biology and Medicine" Clarendon Press, Oxford pp. 136-76 (1989). Hydroxyl radicals are extremely reactive species and could cause the permanent site-specific damage to basement membrane proteins and histopathological changes that are typical of diabetic microvascular disease. See, Robbins S. L., Cotran R. S., Kumar V. "Pathologic basis of disease" $3^{rd}$ ed. W. B. Saunders, pp. 991-1061. (1984).

Similarly, any prolonged increase in fructosamine oxidase activity will cause oxidative stress which could account for the excess risk of macrovascular disease and the 75% increase in mortality seen in patients with diabetes mellitus compared with non-diabetic individuals. Recent studies have convincingly demonstrated that oxidative modification of low density lipoprotein (LDL) is involved in the development of atherosclerosis of coronary and peripheral arterial vessels and elevated oxidized LDL concentrations are found in subjects with diabetes mellitus. See, Witztum J. L. Br Heart J 69 (Suppl): S12-S18 (1993) and Picard S., Talussot C., Serusclat A. et al. Diabetes and Metabolism 22: 25-30 (1996). Oxidative changes to membrane lipids and to membrane protein SH-groups may also cause aberrations in cellular calcium homeostasis and contribute to the increased incidence of cardiac sudden death that is typical of diabetes. See, Yucel D., Aydogdu S., Cehreli S. et al. Clin Chem 44: 148-54 (1998).

Triethylenetetramine dihydrochloride, also known as trienes or trien-2HCl or trientine dihydrochloride, is a copper chelating agent. Trienes have been used for treating individuals with Wilson's disease. See, for example, Dubois R. S., *Lancet* 2 (7676): 775 (1970); Walsh, J. M., *Q J. Med.* 42 (167): 441-52 (1973); Haslam, R. H., et al., *Dev Pharmacol Ther* 1 (5): 318-24 (1980). Trienes have also been used to treat individuals with primary biliary cirrhosis. See, for example, Epstein O., et al., *Gastroenterology* 78 (6): 1442-5 (1980). In addition, trienes have been used to inhibit the spontaneous development of hepatitis and hepatic tumors in rats. See, for example, Sone K., et al., *Hepatology* 23 (4): 764-70 (1996). Thus far, trienes have not been used in the treatment of diabetes.

All publications and patents cited herein are hereby incorporated by reference in their entirety.

BRIEF SUMMARY

Excess fructosamine oxidase activity with glycated basement membrane protein substrate plays a vital role in diabetic complications by the formation of $\alpha$-dicarbonyl and reactive oxygen free radical species.

This damage may be ameliorated by administering specific fructosamine oxidase inhibitors or antagonists selected from the groups: (i) copper chelating agents; (ii) substrate analogues; and (iii) hydrazine compounds.

In one aspect, the present invention consists in a method of treating an individual (human or otherwise) predisposed to and/or suffering from diabetes mellitus with a view to minimizing the consequences of macrovascular and microvascular damage to the patient (e.g., accelerated atherosclerosis, blindness, renal failure, neuropathy, etc.) which comprises, in addition to any treatment in order to control blood glucose levels, at least periodically inhibiting or antagonizing fructosamine oxidase enzyme activity in the patient.

Preferably said inhibition, or antagonism occurs as a result of administration or self-administration of at least one fructosamine oxidase reaction product inhibitor or antagonist.

Preferably any such inhibitor or antagonist is selected from the groups:
(i) copper chelating agents;
(ii) substrate analogue; and/or
(iii) hydrazine compound.

Preferably said inhibitor or antagonist is taken orally.

Preferably said inhibitor or antagonist is taken orally as part of a regime, whether totally oral or not, which also involves the control of blood glucose levels.

In a further aspect, the present invention consists in a pharmaceutical composition (preferably oral) suitable for use in such a method, said composition comprising a fructosamine oxidase inhibitor or antagonist in conjunction with a suitable carrier therefor.

In yet a further aspect, the present invention consists in a pharmaceutical composition for reducing macrovascular and microvascular damage in an individual (including a human) suffering from diabetes mellitus, said composition comprising a fructosamine oxidase inhibitor or antagonist and a suitable carrier therefor.

Preferably said carrier can be any diluent, excipient or the like and the dosage form of said pharmaceutical composition can be of any appropriate type whether for oral or other administration or self-administration. Long acting release forms are also envisaged within the present invention.

In still a further aspect, the present invention consists in the use of a fructosamine oxidase inhibitor or antagonist in the manufacture of a pharmaceutical composition comprising the fructosamine oxidase inhibitor or antagonist and a suitable pharmaceutical carrier therefor and which composition is useful in treating an individual (human or otherwise) which or who is suffering from diabetes mellitus to reduce macrovascular and microvascular damage (preferably by a method of the present invention).

In still a further aspect, the present invention consists in combination, the treatment regimes, and/or the medicaments of such regimes previously set forth whether packed together or prescribed together or otherwise.

In still another aspect, the invention consists in a method of treating an individual (human or otherwise) predisposed to and/or suffering from diabetes mellitus, which includes inhibiting or antagonizing fructosamine oxidase enzyme activity in the patient with an agent or agents preferably not contraindicated for the patient. Examples of inhibitors or antagonists include but are not limited to those listed hereinafter.

Preferably in one embodiment said agent(s) is or are copper chelating compound(s) administered or self-administered to the patient.

Examples of suitable copper-chelating compounds include triethylenetetramine dihydrochloride, penicillamine, sar, diamsar, ethylenediamine tetraacetic acid, o-phenanthroline, and histidine.

Preferably in another embodiment, said agent(s) is or are substrate analogue compound(s) administered or self-administered to the patient having an amino acid or peptide moiety with a blocked N-terminal amine group.

Examples of a suitable substrate analogue composition are N-acetylcysteine, captopril, lisinopril and enalapril.

Preferably in another embodiment said agent(s) is or are hydrazine compound(s) administered or self-administered to the patient i.e., a compound having a —$NHNH_2$ moiety.

Examples of a suitable hydrazine compound include diaminoguanidine, hydralazine, and carbidopa.

In still another aspect, the invention consists in a dosage regimen for a method of the present invention and/or using dosage units of the present invention.

In still a further aspect, the present invention consists in the use of pharmaceutically acceptable compounds being at least one of a substrate analogue, a hydrazine compound and a copper chelator in the manufacture of a dosage unit or pharmaceutical composition useful in treating an individual (human or otherwise) which or who is suffering from diabetes mellitus to reduce macrovascular and microvascular damage.

In another aspect, the invention consists in a dosage unit or pharmaceutical composition for an individual useful in a method of the present invention comprising (preferably in effective fructosamine oxidase reaction product-inhibiting or -antagonizing amounts -separately or collectively) of a compound (or compounds) being a substrate analogue or a hydrazine compound having an —NHNH$_2$ moiety, or both.

Preferably said dosage unit also includes said pharmaceutical composition that also includes one or more compounds which are copper chelators.

Preferably said dosage unit or composition is in an oral dosage form optionally with carriers, excipients or, indeed, even other active agents (e.g., means to lower blood glucose levels).

In still another aspect, the invention consists in a regime or dosage unit or pharmaceutical composition for a diabetic or suspected diabetic individual of the copper chelator, triethylenetetramine dihydrochloride, providing for the patient a sufficient fructosamine oxidase inhibiting and/or antagonizing effect to reduce macrovascular and microvascular damage.

In still another aspect, the invention consists in a regime or dosage unit or pharmaceutical composition of captopril for a diabetic or suspected diabetic individual, whether effective or intended to be effective in controlling the blood pressure of the diabetic patient (at least in part) or not, providing for the patient a sufficient fructosamine oxidase inhibiting and/or antagonizing effect to reduce macrovascular and microvascular damage.

In yet another aspect, the invention consists in a regime or dosage unit or pharmaceutical composition for a diabetic patient or suspected diabetic patient of a hydrazine compound providing for the patient a sufficient fructosamine oxidase inhibiting and/or antagonizing effect to reduce macrovascular and microvascular damage.

In yet another aspect, the invention consists in a regime or dosage unit or pharmaceutical composition for a diabetic patient or suspected diabetic patient of (i) acetylcysteine and (ii) at least one other fructosamine oxidase inhibitor and/or antagonist, the mix of (i) and (ii) providing for the patient a sufficient fructosamine oxidase inhibiting and/or antagonizing effect to reduce macrovascular and microvascular damage.

In yet another aspect, the invention consists in a regime or dosage unit or pharmaceutical composition for a diabetic patient or suspected diabetic patient of (i) hydralazine and (ii) at least one other fructosamine oxidase inhibitor and/or antagonist, the mix of (i) and (ii) providing for the patient a sufficient fructosamine oxidase inhibiting and/or antagonizing effect to reduce macrovascular and microvascular damage.

In still another aspect, the present invention consists in a method of treating an individual (human or otherwise) predisposed to and/or suffering from diabetes mellitus which includes inhibiting and/or antagonizing fructosamine oxidase enzyme activity in the patient with acetylcysteine and hydralazine.

In still another aspect, the invention consists in a regime or dosage unit or pharmaceutical composition for a diabetic or suspected diabetic individual which includes acetylcysteine and hydralazine.

In still a further aspect, the present invention consists in the use of or co-administration or serial administration of acetylcysteine and hydralazine for the purpose of reducing macrovascular and microvascular damage in an individual.

Preferably said individual is diabetic.

In yet another aspect, the invention consists in a method of treating and/or reducing the likelihood of diabetic cataract formation in an individual which comprises at least periodically inhibiting and/or antagonizing fructosamine oxidase enzyme activity in the mammal.

Preferably the method involves the administration or self-administration of effective amounts of triethylenetetramine dihydrochloride (or other triene).

In another aspect, the invention consists in a method of treating and/or reducing the likelihood of diabetic cardiomyopathy in an individual which comprises at least periodically inhibiting and/or antagonizing fructosamine oxidase enzyme activity in the individual.

Preferably the method involves the administration or self-administration of effective amounts of triethylenetetramine dihydrochloride (or other triene).

Preferably for any of the aforesaid indications triethylenetetramine dihydrochloride (or other triene) is administered and/or self administered in concert with another (other) fructosamine oxidase enzyme inhibitor(s) and/or antagonist(s).

Preferably said another inhibitor and/or antagonist or said other inhibitors and/or antagonists is or are administered or self administered to elicit a pharmacological effect for another indication yet together with the effect of the triene is or are in an amount or amounts which are effective for treating or ameliorating macrovascular and microvascular damage of such an individual.

Reference is drawn to PCT Application PCT/NZ99/00161, filed Sep. 24, 1999 (claiming priority of New Zealand Patent Specification No. 332085 filed Sep. 25, 1998), the full content of which is hereby incorporated by reference. It discloses methods of monitoring fructosamine oxidase inhibition and/or antagonism of patients, screening patients to determine patients at risk to vascular (particularly microvascular) damage and identifying those individuals who will benefit by treatment with fructosamine oxidase inhibitors and/or antagonists, methods of determining fructosamine oxidase levels in a mammal, methods of determining blood plasma fructosamine oxidase levels in a diabetic individual or a suspected individual, methods of assaying blood serum or blood plasma in vitro for fructosamine oxidase, methods of identifying or testing candidate substances and to related methods and procedures.

Preferably the measurement conducted in vitro is of the superoxide reaction product (or any other oxygen free radical product) of fructosamine oxidase.

DETAILED DESCRIPTION

Figure 1:
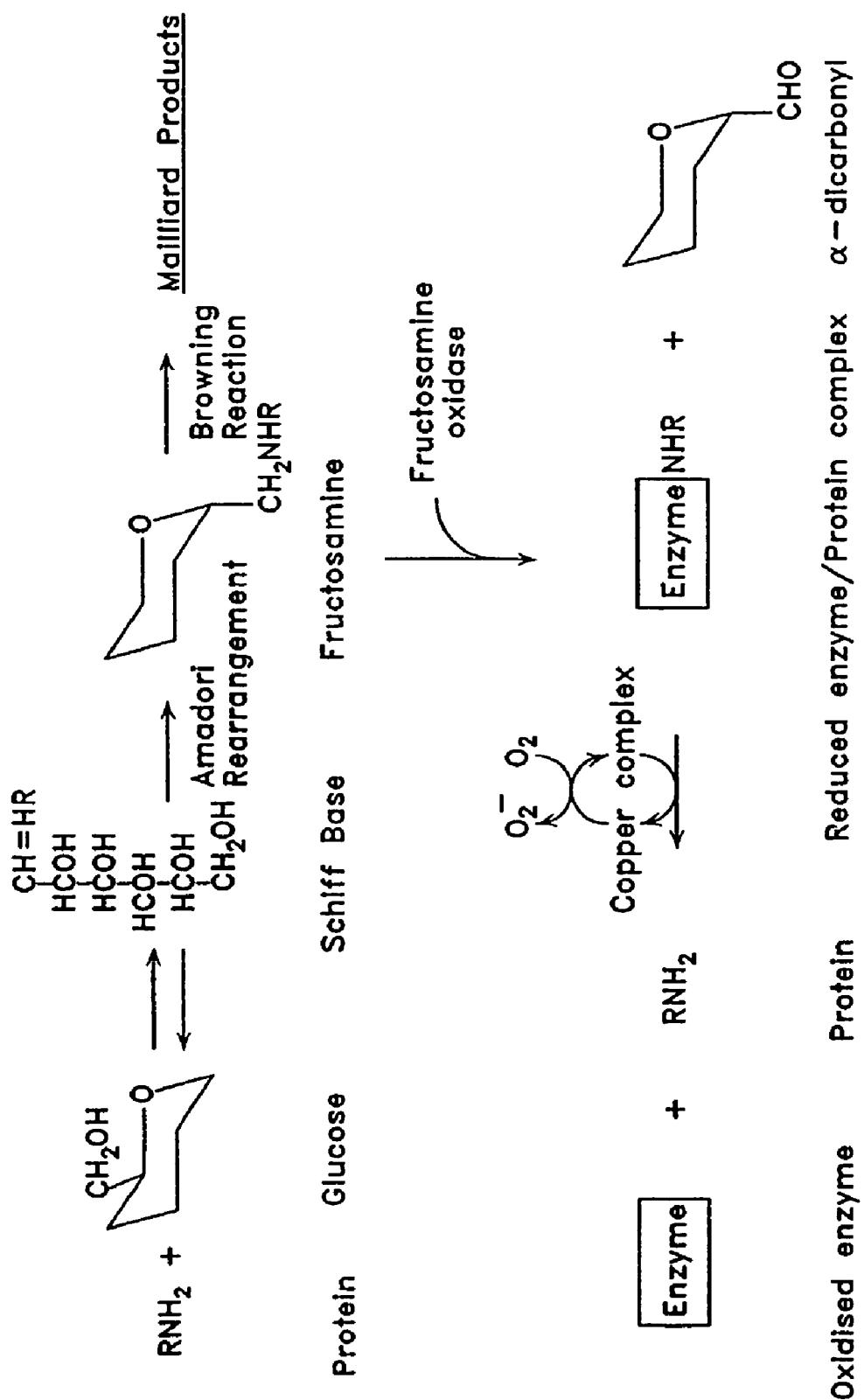
FIG. 1 shows a detailed reaction mechanism for the formation of fructosamine and Maillard products from glucose and protein. Fructosamine oxidase degrades fructosamine by a two-step reaction with initial release of an α-dicarbonyl sugar and subsequent oxidation of the enzyme/protein complex to release free unglycated protein. The reduced copper cofactor is oxidized in vivo by molecular oxygen and the oxidation product is superoxide.

The present invention discloses the use of fructosamine oxidase inhibitors to treat an individual with diabetes mellitus. In one aspect, the invention provides methods of treating diabetes by reducing fructosamine oxidase activity within an individual who is suffering from diabetes.

Definitions

As used herein (including in the claims), the term "inhibitor" is used interchangeably with "antagonist" and refers to a compound which substantially reduces fructosamine oxidase activity.

The term "substantially reduces" refers to a reduction of fructosamine oxidase activity by about 5%, more preferably about 10%, even more preferably about 20%, even more preferably about 30%, even more preferably about 40%, even more preferably about 50%, even more preferably about 60%, even more preferably about 70%, even more preferably about 80%, even more preferably about 90%, even more preferably about 100%.

The term "copper chelating agents" means any agent which reduces body fructosamine oxidase activity by lessening the availability of body copper stores and/or by the binding of said copper chelating agent to fructosamine oxidase enzyme. Such binding can have various effects, for example, inactivation of the copper molecule at the reactive center of the enzyme, conformational changes that may affect the activity of the enzyme, or binding a non-reactive portion of the enzyme in a manner that affects the activity of the enzyme. Binding can be either reversible or irreversible.

The term "substrate analogue" refers to any chemically modified amino acid or peptide substrate which lessens the activity of fructosamine oxidase enzyme. A non-limiting example by which a substrate analogue can lessen the activity of fructosamine oxidase is by binding to the enzyme. Such binding can have various effects, for example, inactivation of the reactive center of the enzyme, conformational changes that may affect the activity of the enzyme, or binding a non-reactive portion of the enzyme in a manner that affects the activity of the enzyme. Binding can be either reversible or irreversible.

The term "hydrazine compound" means any agent containing the moiety —NH—NH$_2$ which lessens the activity of fructosamine oxidase enzyme. A non-limiting example by which a hydrazine compound can lessen the activity of fructosamine oxidase is by binding to the enzyme. Such binding can have various effects, for example, inactivation of the reactive center of the enzyme, conformational changes that may affect the activity of the enzyme, or binding a non-reactive portion of the enzyme in a manner that affects the activity of the enzyme. Binding can be either reversible or irreversible.

The term "at least periodically" includes from a single administration to continuous administration.

The term "macrovascular damage" refers to accelerated atherosclerosis of large arteries supplying blood to the heart, to the lower limbs, and to the brain. Macrovascular damage can be assessed by various organ imaging techniques such as catheter/dye studies (angiograms) and magnetic resonance angiography. Furthermore, in animal models, whole body responses include, but not limited to, survival and/or weight gain and/or histopathological changes of cardiomyopathy can also be used to assess macrovascular damage. In humans, macrovascular damage can be assessed by any of the measured above as well as monitoring significant physiological changes seen during clinical trial of different fructosamine oxidase inhibitors.

The term "microvascular damage" refers to damage to small arterioles and capillaries, for example, the arterioles and capillaries supplying blood to the retina in the eye, the glomerulus in the kidney, and the peripheral and autonomic nervous system. Microvascular damage of the retina can be assessed by direct ophthalmoscopy, by slit lamp microscopy, or by fluorescein angiography. Microvascular damage elsewhere may be assessed by surrogate measurements. For example, microvascular damage to the kidney glomerulus or peripheral nerves can be assessed by its effect on tissue function, e.g., proteinuria reflects damage to the kidney glomerulus or nerve conduction studies reflect damage to peripheral nerves.

"In concert with" does not necessarily mean as a result of simultaneous administration or self-administration. It can be administered serially and such serial application can be spaced, i.e., a triene between meals and another agent with a meal.

The terms "triethylenetetramine dihydrochloride" and "triene" are used interchangeably throughout and includes any pharmaceutically acceptable fructosamine oxidase enzyme inhibiting and/or antagonizing analogue or metabolite thereof (e.g., an acetylated derivative) for the target mammalian species or for a human being capable of administration or self administration in an amount alone or in concert with another fructosamine oxidase enzyme inhibitor and/or antagonist (preferably not contraindicated by toxicity concerns having regard to levels required for effective inhibition and/or antagonism), of providing effective inhibition and/or antagonism.

The term "an effective amount" of a fructosamine oxidase inhibitor refers to the amount of one or more fructosamine oxidase inhibitors required to ameliorate the physiological well-being of an individual suffering from diabetes mellitus. This can involve the amount having an effect on fructosamine oxidase activity in an individual to which the inhibitor(s) is being administered.

An "individual" is a vertebrate, preferably a mammal, more preferably a human. Mammals include, but are not limited to, humans and non-rodent pets.

"Comprises" can mean "includes".

"And/or" means both "and" and "or".

Use of Fructosamine Oxidase Inhibitors

Fructosamine oxidase inhibitors can be selected from any number of compounds from several different groups such as copper chelators, substrate analogs, and hydrazine compounds. These compounds are readily available from commercial sources, for example, Sigma Chemical Company (St Louis, Mo.) or Aldrich Chemicals Milwaukee, Wis.). Preferably the compound is a triene. The triene can be administered by any appropriate administration route. Non-limiting examples include oral intake (i.e., ingestion by eating or drinking), injection, and mucosal. In one embodiment, a triene is administered in a pharmaceutically acceptable composition. In another embodiment, a triene is used as a pharmaceutically acceptable composition in combination with another compound to lessen fructosamine oxidase activity. Preferably the combination of the triene and a second compound act in cooperation with each other to lower fructosamine oxidase activity. In yet another embodiment, a combination of at least two fructosamine oxidase inhibitors are used in a pharmaceutically acceptable composition. Preferably, the inhibitors do not lessen the efficacy of each other when administered in combination. Preferably, a triene is administered with a pharmaceutically acceptable excipient. A pharmaceutically acceptable excipient is a relatively inert substance that facilitates administration of a pharmacologically effective substance. For example, an excipient can give form or consistency to the vaccine composition, or act as a diluent. Suitable excipients include but, are not limited to stabilizing agents, wetting and emulsifying agents, salts for varying osmolarity, encapsulating agents, buffers, and skin penetration enhancers. Examples of pharmaceutically acceptable excipients are described in Remington's Pharmaceutical Sciences, Alfonso R. Gennaro, ed., 18th edition, (1990). The dosage used is an effective amount of a fructosamine oxidase inhibitor to substantially reduce fructosamine oxidase activity. Preferably, the dosage used is an effective amount of a triene to substantially reduce fructosamine oxidase activity. In an alternate embodiment, the dosage used is an effective amount to substantially reduce the symptoms of diabetes and its sequelae (renal dysfunction, visual dysfunction, cardiovascular disease, wound healing problems, etc.). The dosage is preferably about 1 mg/kg to about 1 g/kg, more preferably about 2 mg/kg to about 800 mg/kg, even more preferably about 5 mg/kg to about 600 mg/kg, even more preferably about 7 mg/kg to about 400 mg/kg, even more preferably about 9 mg/kg to about 200 mg/kg, even more preferably about 11 mg/kg to about 100 mg/kg, even more preferably about 13 mg/kg to about 75 mg/kg, even more preferably about 15 mg/kg to about 50 mg/kg, even more preferably about 17 mg/kg to about 35 mg/kg. The administration can be as often as needed to achieve a reduction in fructosamine oxidase activity. A skilled artisan may determine if the combination lessens the efficacy by a stepwise administration of a combination of fructosamine oxidase inhibitors at various dosages and measuring parameters exemplified in the Examples such as weight loss, etc. Fructosamine oxidase inhibitors, preferably a triene alone or in combination with other inhibitors, can be administered to individual suffering from diabetes mellitus and its sequelae and/or to individuals who are susceptible to diabetes mellitus (i.e., genetic pre-disposition). Genetic pre-disposition can be determined by examination and analysis of family history of diabetes mellitus or by genetic markers correlated with development of diabetes mellitus.

EXAMPLES

Example 1

Extraction of Holoenzyme

Fructosamine oxidase in blood plasma is largely found as an enzyme-substrate conjugate, bound to peptides and proteins (FIG. 1). To obtain a maximal yield of active holoenzyme, it was necessary to make the pH of the media alkaline preferably with phosphate buffer, to add sulphydryl reagents, and to incubate the mixture with pro-oxidant so that glycated species were released. Most effective activation was found with cupric salts.

Fructosamine oxidase holoenzyme was separated from inactive apoenzyme by affinity adsorption chromatography. A suitable glycated affinity support was prepared from alkylamine beads or beaded cross-linked agarose with amino terminal residues attached by 6-10 atom spacer arms (available from Pierce™, Bio-Rad™, and Pharmacia™). The affinity support was glycated by incubating with 400 mM potassium phosphate buffer pH 7.4 containing 50 mM glucose and 0.01% sodium azide at 37° C. for 7 days. Holoenzyme bound tightly to glycated amino residues and residual copper was readily removed by washing with water. Active holoenzyme was eluted with 800 mM NaCl in 50 mM sodium acetate buffer pH 4.8. Active fractions were pooled and protein was precipitated with 50% cold acetone solvent. The protein pellet was reconstituted with a minimum volume of water or physiological saline and lyophilized for long term storage.

Fructosamine oxidase holoenzyme was separated from inactive apoenzyme by affinity adsorption chromatography. A suitable glycated affinity support was prepared from alkylamine beads or beaded cross-linked agarose with amino terminal residues attached by 6-10 atom spacer arms (available from Pierce™, Bio-Rad™, and Pharmacia™). The affinity support was glycated by incubating with 400 mM potassium phosphate buffer pH 7.4 containing 50 mM glucose and 0.01% sodium azide at 37° C. for 7 days. Holoenzyme bound tightly to glycated amino residues and residual copper was readily removed by washing with water. Active holoenzyme was eluted with 800 mM NaCl in 50 mM sodium acetate buffer pH 4.8. Active fractions were pooled and protein was precipitated with 50% cold acetone solvent. The protein pellet was reconstituted with a minimal volume of water or physiological saline and lyophilized for long term storage.

Figure 2:
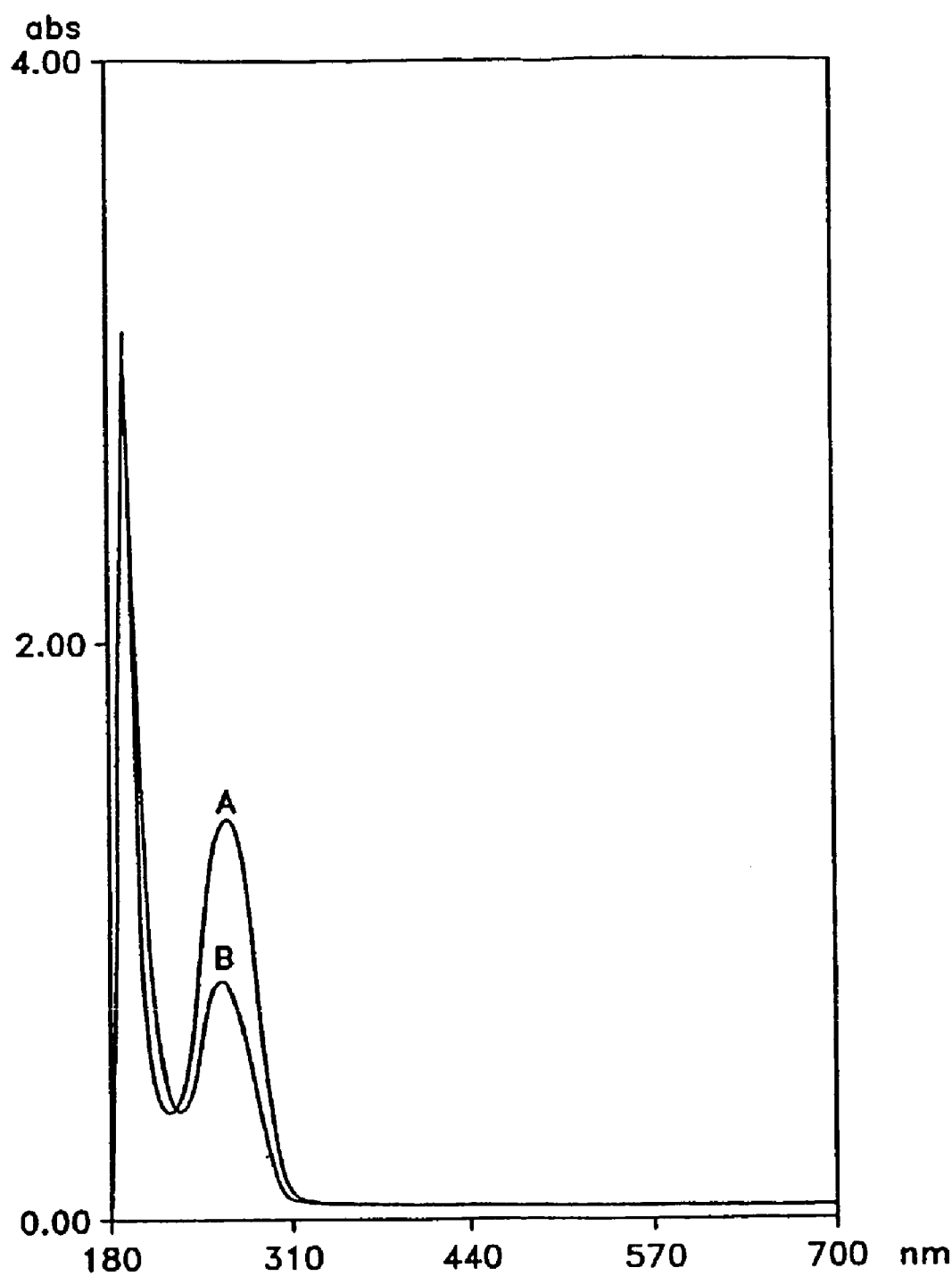
FIG. 2 shows the absorbance spectra of the fructosamine oxidase enzymes extracted from pooled human sera (A) and from the microbial organism, *Enterbacter aerogenes* (B).
Figure 3:
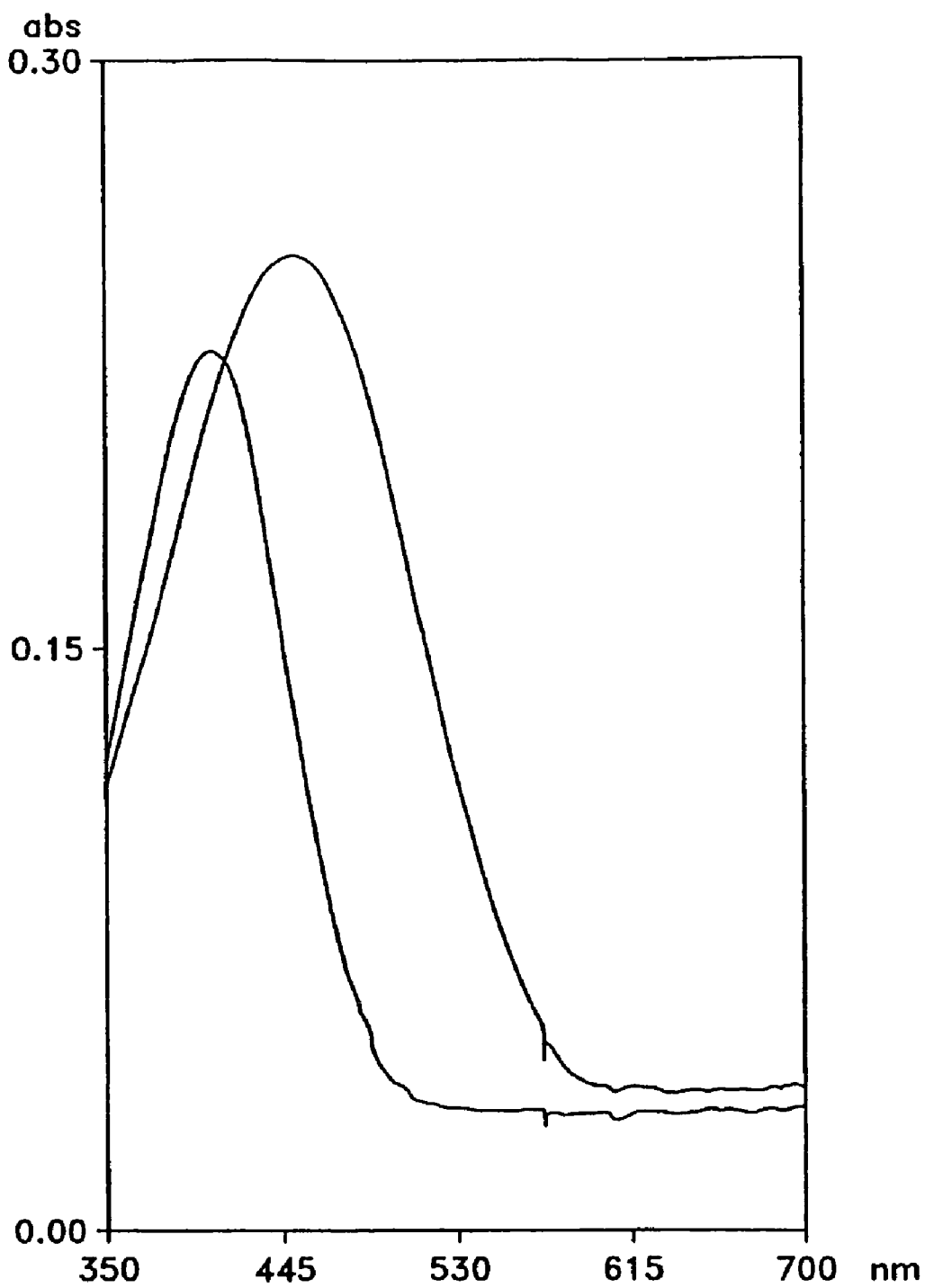
FIG. 3 shows the spectra of p-nitrophenylhydrazine (NPH) adduct of the *Enterbacter aerogenes* enzyme (A) and a red absorbance shift when the NPH-enzyme adduct is diluted in 2M KOH.

Extraction of 35 mL pooled diabetic and non-diabetic human sera yielded a clear colorless preparation with absorbance peaks at 196 nm and 264 nm typical of the absorbance spectra of fructosamine oxidase (FIG. 2). A fructosamine oxidase enzyme from *Enterobacter aerogenes* showing absorbance peaks at 196 nm and 255 nm was included for comparison. Enzyme activity and relative activity was as follows.

TABLE I

| Sample | Protein (µg/mL) | Cytochrome c activity* (U/L) | Sp activity† (U/g) |
|---|---|---|---|
| human | 32.9 | 4.58 | 139.4 |
| E. aerogenes | 541.5 | 66.32 | 115.11 |

*Enzyme extract was preincubated in 0.05 M TES buffer pH 7.4 containing 1 mM DMF substrate at 37° C. for 5 minutes. Enzyme activity was measured with 10 µM ferricytochrome c. The reaction was started with 50 µM fructosamine substrate as g-BSA and $\Delta A_{550\,nm}$ was determined over 5 minutes.
†Protein concentration determined from $A_{210\,nm}$-$A_{220\,nm}$ compared with BSA standards.

Cofactor Identification

The p-nitrophenylhydrazine (NPH) adduct of *Enterbacter aerogenes* enzyme with $A_{max}$ 399 nm was obtained as described previously. See, Palcic M. M., Janes S. M. *Meth Enzymol* 258: 34-8 (1995). A red absorbance shift to $A_{max}$ 438 nm was observed when the NPH-enzyme adduct was diluted in 2M KOH. Such an absorbance shift was typical of the quinone cofactors of copper amine oxidase.

Example 2

Identifying Fructosamine Oxidase Inhibitors

The purpose of this example was to demonstrate how the fructosamine oxidase assay, the subject of a PCT International patent specification NZ 332085 the contents of which are hereby incorporated by reference, may be used in identifying and grading candidate fructosamine oxidase inhibitors. This approach took into account the activity of the drug in a human plasma matrix in vitro. Enzyme inhibitors have wide and numerous applications in clinical medicine as treatments for a range of metabolic disorders. For example, angiotensin converting enzyme inhibitors have been used in the treatment of hypertension. See, for example, Harris E. E., Patchett A. A., Tristram E. W., and Wyvratt M. J., "Aminoacid derivatives as antihypertensives" U.S. Pat. No. 4,374,829 (1983). Similarly, 3-hydroxy-3-methylglutaryl-coenzyme A (HMG-CoA) reductase enzyme inhibitors have been used in the treatment of hypercholesterolemia. See, for example, Hoffman W. F., Smith R. L., Lee T. J., "Novel HMG-CoA reductase inhibitors" U.S. Pat. No. 4,866,090 (1989). Fructosamine oxidase inhibitors may be selected from those substances which bind and block the quinone co-factor (hydrazine compounds), the copper co-factor (copper chelators), or which mimic the normal substrate of the enzyme (substrate analogue).

Method:

Potential fructosamine oxidase inhibitors were tested on human serum or plasma individually and in combination) using the method of assaying fructosamine oxidase activity described in detail in a New Zealand Patent Specification No. 332085. Irreversible enzyme inhibition was characterized by a progressive decrease in activity with time ultimately reaching complete inhibition even with very dilute inhibitor concentrations provided that the inhibitor is in excess of the amount of enzyme present.

Results:

The relative activity of a selection of hydrazine, copper chelator, and substrate analogue Fructosamine oxidase inhibitors are shown in Table 2. In some instances, there was a degree of overlap between classes, i.e., some hydrazine compounds were also copper chelators. To clarify this point, the copper chelating potential for some compounds is indicated ($\beta$). The effectiveness of the inhibitor was expressed not by an equilibrium constant but by a velocity constant (K) which determined the fraction of the enzyme inhibited in a given period of time by a certain concentration of inhibitor. The specificity of the inhibitor for the active center of the enzyme was indicated by the concentration of inhibitor causing 50% inactivation of the enzyme ($IC_{50}$).

TABLE 2

|  | $IC_{50}$[1] | $K(min^{-1})$ | $\beta$[3] |
|---|---|---|---|
| Inhibitor: Hydrazine compounds |  |  |  |
| aminoguanidine | 231 μM | 0.0067* | — |
| semicarbazide | 45 μM | 0.0276* | +++ |
| benserazide | 13.6 μM | 0.0095* |  |
| oxalic dyhydrazide | 1.59 μM | 0.0542 | — |
| hydralazine | 1.52 μM | 0.0029 | +++ |
| phenylhydrazine | 0.81 μM | 0.1160 |  |
| carbidopa | 0.50 μM | 0.1496 |  |
| diaminoguanidine | 0.36 μM | 0.1340 | — |
| Inhibitor: Substrate analogues |  |  |  |
| lisinopril | 216.9 μM | 0.0174 | +++ |
| enalapril | 3.95 μM | 0.0326 | — |
| captopril | 1.78 μM | 0.0259 |  |
| acetylpenicillamine | 1.06 μM | 0.0811 |  |
| acetylcysteine | 0.83 μM | 0.1677 |  |
| Inhibitor: Copper chelators |  |  |  |
| desferrioxamine | 40.6 μM | 0.0109* |  |
| EDTA | 15.7 μM | 0.0755* |  |
| Sodium azide | 9.48 μM | 0.0004 |  |
| Potassium cyanide | 6.36 μM | 0.0116 |  |
| triethylenetetramine dihydrochloride | 5.40 μM | 0.0196 |  |

TABLE 2-continued

|  | $IC_{50}$[1] | $K(min^{-1})$ | $\beta$[3] |
|---|---|---|---|
| o-phenathroline | 4.25 μM | 0.0385 |  |
| histidine | 2.29 μM | 0.0554 |  |
| Inhibitor: Combined agents |  |  |  |
| acetylcysteine + hydralazine | 0.57 μM | 0.1654 |  |
| acetylcysteine + diamino guanidine | 1.07 μM | 0.0795 |  |
| acetylcysteine + histidine | 1.11 μM | 0.0722 |  |
| acetylcysteine + carbidopa | 0.27 μM | 0.2000 |  |

[1]fresh human sera was incubated with 0-1,000 μM inhibitor in 0.05 M TES buffer pH 7.4 at 37° C. for 5 minutes. Enzyme activity was measured with 10 μM ferricytochrome c. The reaction was started with 50 μM fructosamine substrate as g-BSA and $\Delta A_{550\,nm}$ was determined over 5 minutes
[2]rate constants were calculated from the reaction of fructosamine oxidase either with 1.0 μM inhibitor or with 10.0 μM inhibitor (*)
[3]the copper chelating potential ($\beta$) was determined from the ability of the agent to remove copper under dialysis from copper-saturated BSA substrate.

Conclusions:

Irreversible inhibition of fructosamine oxidase is feasible.

Inhibitors may be broadly categorized in three classes of compound: hydrazines; substrate analogues; and copper chelators.

Fructosamine oxidase activity in human blood plasma may be eliminated by micromolar concentrations of inhibitors.

Many of the active inhibitors are drugs which have already been administered as medicines in humans to treat other disorders (not diabetes).

Example 3

First Preclinical Study

The purpose of this example was to demonstrate how the clinical usefulness of candidate fructosamine oxidase inhibitors may be assessed using a standard animal model of diabetes mellitus, the streptozocin-diabetic rat (STZ rat). This approach took into account drug bioavailability, the activity of the drug and its metabolites, and any drug adverse effects or toxicity factors.

Method:

48 Wistar rats aged 6-8 weeks and weighing 200-300 g were randomized:

Group 1 Non-diabetic control
Group 2 Diabetic control
Group 3 Diabetic treated with hydralazine
Group 4 Diabetic treated with EDTA
Group 5 Diabetic treated with hydralazine and acetylcysteine
Group 6 Diabetic treated with acetylcysteine Streptozotocin (60 mg per kg) was administered into a lateral tail vein.

Non-diabetic controls received a sham injection of buffer. Diabetes was confirmed by venous blood glucose measurement >15 mmol/L after 1 week and diabetic animals were treated with subcutaneous injections of ultralente insulin (4 U/injection) 3-5 days per week to maintain body growth. Medications were administered 50 mg/L in the drinking water over an 8-month period. Timed urine collections and venous plasma samples were obtained at monthly intervals.

Results:

Blood glucose control: Rate of conversion to diabetes with intravenous STZ administration was >95%. Intravenous STZ induced a severe form of insulin-dependent diabetes which was sustained over the entire 8-month duration of the study Despite insulin replacement therapy, glycemia control was poor as evidenced by mean±SD glucose (week 4) and $HbA_{1c}$ (week 32) levels in Table 3.

TABLE 3

|  | Group 1 | Group 2 | Group 3 | Group 4 | Group 5 | Group 6 |
|---|---|---|---|---|---|---|
| Glucose (mmol/L) | 9.1 ± 1.5 | 30.1 ± 9.7 | 35.7 ± 9.5 | 39.0 ± 6.04 | 30.4 ± 8.8 | 37.8 ± 5.2 |
| $HbA_{1c}$(%) | 3.82 ± 0.11 | 10.85 ± 0.05 | 8.65 ± 1.18 | 9.30 ± 0.63 | 8.72 ± 0.55 | 9.47 ± 1.23 |

(b) Survival: Mortality rate amongst untreated STZ rats was extremely high. Survival was improved significantly by the administration of fructosamine oxidase inhibitors (Table 4).

TABLE 4

|  | Group 1 | Group 2 | Group 3 | Group 4 | Group 5 | Group 6 |
|---|---|---|---|---|---|---|
| Survivors at week 32 | 8 | 2 | 6 | 5 | 8 | 7 |
| Significance* | — | — | ns | ns | $P < 0.025$ | $P < 0.05$ |

*Chi-square test compared with untreated STZ rats (Group 2)

Figure 4:
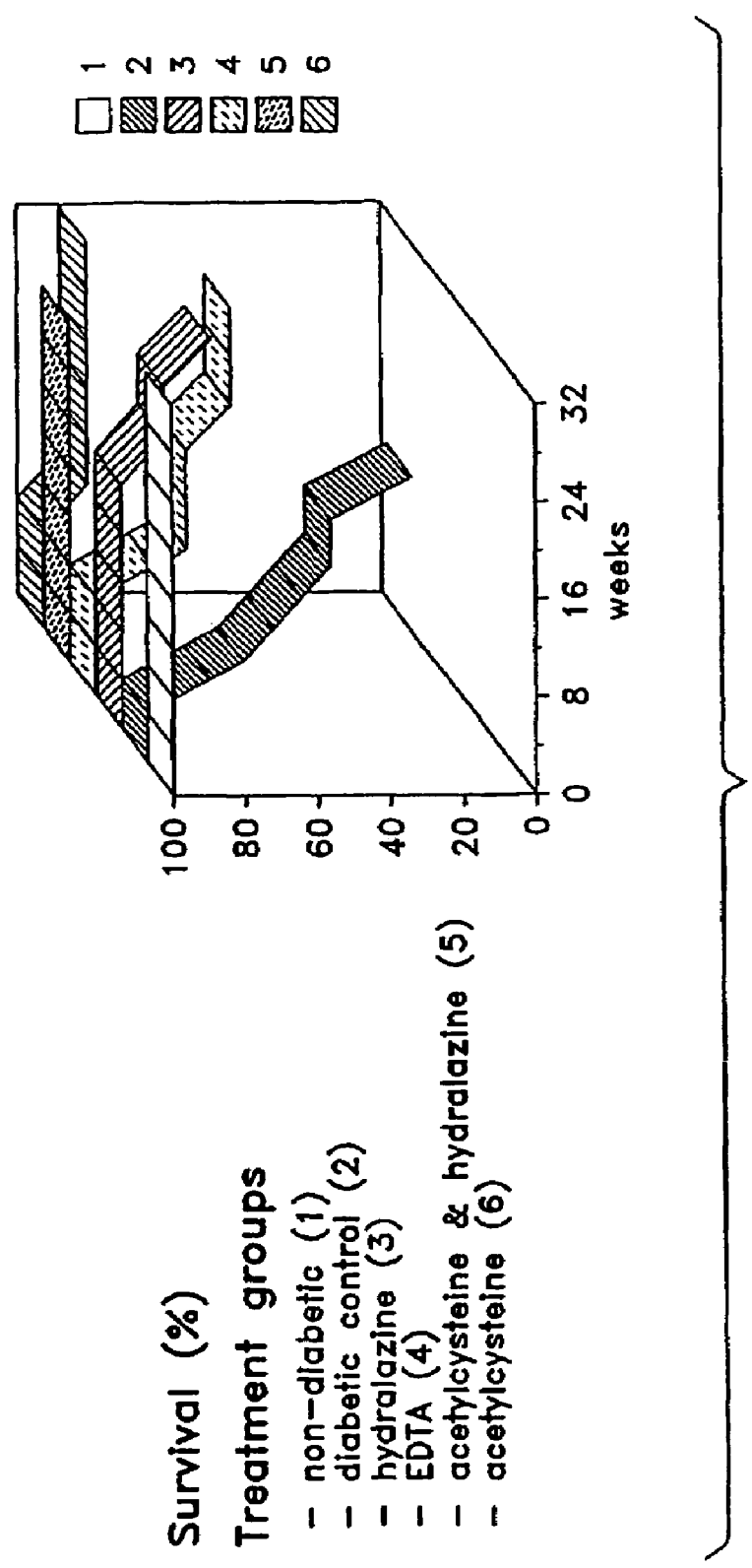
FIG. 4 shows the survival curve for non-treated STZ-diabetic rats compared with diabetic animals treated with fructosamine oxidase inhibitors.

The survival curve for STZ rats compared with non-diabetic controls is shown in FIG. 4. Death was presumed secondary to a cardiovascular event. In general, renal function remained normal.

Figure 5:
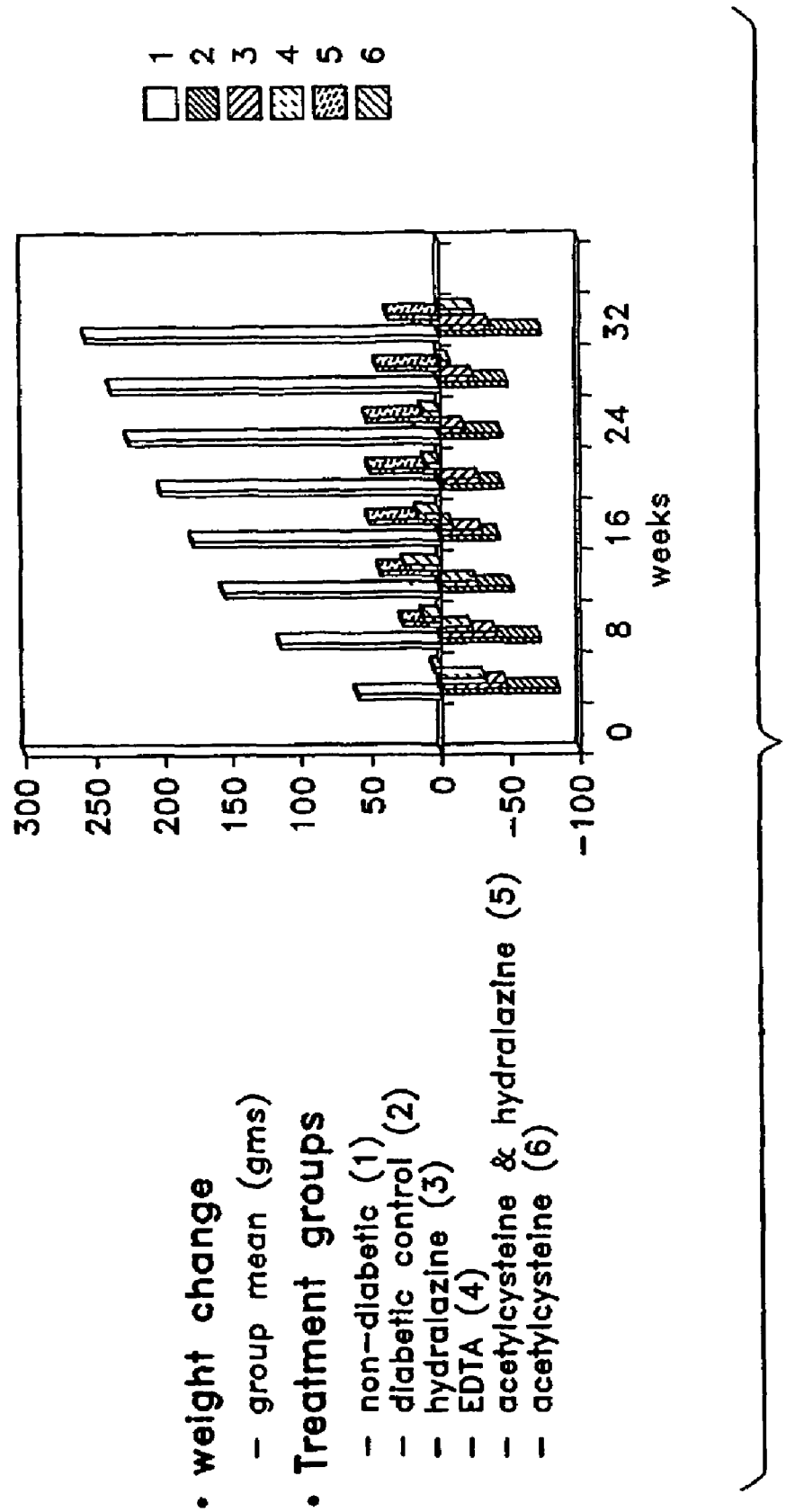
FIG. 5 shows the monthly growth of treated and untreated STZ-diabetic rats compared with non-diabetic animals.

(c) Weight gain: There was a progressive weight gain amongst non-diabetic controls over the 32 weeks of the study which was abolished in the STZ diabetic animals. At the end of the 32 week study period, mean weight change amongst surviving study animals was: Group 1, +74.6%; Group 2, −21.0%, Group 3, −11.0%; Group 4, +1.2%, Group 5, +16.0%; and Group 6, −8.1% (FIG. 5). Compared with untreated diabetic controls, fructosamine oxidase inhibitors caused an improvement in weight gain roughly in proportion to the activity of the inhibitor (Table 2), i.e., acetylcysteine/hydralazine>EDTA>acetylcysteine>hydralazine.

(d) Clinical Pharmacokinetics:

Hydralazine

The bioavailability of hydralazine in man after oral administration is 26-55%. However, only 2.0-3.6% of the drug is excreted in the urine unchanged over 24 hours after oral administration. Most of the drug is recovered as an inactive acetylated product. See, Talseth T., Eur J Clin Pharmacol 10: 395-401 (1976) and Talseth T., Clin Pharmacol Ther 21: 715-20 (1977). This could account for the reduced efficacy of hydralazine as a fructosamine oxidase inhibitor in the current study. Furthermore, drug doses administered to each STZ rat were calculated as 12.5 mg hydralazine/day or 35 mg/kg, based on an average consumption of 250 mL of water per day and assuming a mean body mass of 350 g. This rat dose far exceeds the maximum recommended human dose of 200 mg hydralazine per day (3 mg/kg assuming a mean body mass of 70 kg).

EDTA

The bioavailability of EDTA after oral administration is very low (less than 5%) because of poor absorption from the gut limiting its usefulness in humans to parenteral administration or irrigation techniques. See, for example, Wynn J. E. et al. *Toxicol Appl Pharmacol* 16: 807-17 (1970).

Acetylcysteine

Acetylcysteine is rapidly absorbed from the gut with a bioavailability in man varying between 6 and 10%. See, for example, Borgstrom L. et al. Eur J Clin Pharmacol 31: 217-22 (1986). However, the drug is rapidly degraded in the liver by elimination of the acetyl moiety. See, for example, Holdiness M. R., Clin Pharmacokinet 20: 123-34 (1991). Induction of liver enzymes could account for the progressive loss of drug efficacy seen after week 12 in the current study.

Conclusions:

Streptozocin induces a severe form of Type I diabetes in the rat with a high morbidity and mortality.

Survival of STZ rats was enhanced by treating with fructosamine oxidase inhibitors in proportion to their activity in an in vitro assay.

Weight gain of STZ rats was enhanced by treating with fructosamine oxidase inhibitors.

There was some benefit in co-administering acetylcysteine and hydralazine suggesting a synergy effect between classes of fructosamine oxidase inhibitors.

Based on these in vivo studies in the rat, the efficacy of a candidate fructosamine oxidase inhibitor, for example, in a human is likely to be influenced by the bioavailability of the drug, degradation of the active compound in vivo, and the maximum oral tolerated dose of the drug.

Example 4

Second Preclinical Study

The purpose of this example was to demonstrate how the clinical usefulness of candidate fructosamine oxidase inhibitors, alone and in combination, may be assessed using a standard animal model of diabetes mellitus, the streptozocin-diabetic rat (STZ rat). This approach took into account drug bioavailability, the activity of the drugs and their metabolites, interactions between drugs, and any drug adverse effects or toxicity factors.

Method:

80 Wistar rats weighing 200-300 g and aged of 6-8 weeks were randomized:

Group 1 Non-diabetic control

Group 2 Diabetic control

Group 3 Diabetic treated with captopril (substrate analogue)

Group 4 Diabetic treated with carbidopa (hydrazine)

Group 5 Diabetic treated with triethylenetetramine dihydrochloride (copper chelator)

Group 6 Diabetic treated with captopril and triethylenetetramine dihydrochloride Group 7 Diabetic treated with captopril and carbidopa Group 8 Diabetic treated with triethylenetetramine dihydrochloride and carbidopa.

Diabetes was induced by administering streptozotocin (60 mg per kg) by intraperitoneal injection. Non-diabetic controls received a sham injection of buffer. Diabetes was confirmed by venous blood glucose measurement >15 mmol/L after 1 week and diabetic animals were treated with subcutaneous injections of ultralente insulin (4 U/injection) 3 days per week to maintain body growth. Medications were administered at a concentration of 50 mg/L in the drinking water over a 6-month period. Timed urine collections and venous plasma samples were obtained at monthly intervals. Animals were monitored for blood glucose control and survival rate over the course of study. Animals were sacrificed and subjected to post-mortem examination at the end of the study to determine various parameters of fructosamine oxidase activity inhibitor efficacy. Parameters include, but are not limited to, survival rate, weight gain, cataract formation, and cardiomyopathy.

Results:

Blood glucose control: Rate of conversion to diabetes with intraperitoneal STZ administration was approximately 80%. Poor glycemic control was sustained over the 6 month duration of the study as evidenced by mean±SD $HbA_{1c}$ (week 4, 12, and 24) levels (Table 5).

TABLE 5

| $HbA_{1c}$ | Group 1 | Group 2 | Group 3 | Group 4 | Group 5 | Group 6 | Group 7 | Group 8 |
|---|---|---|---|---|---|---|---|---|
| Week 4 | 4.1 ± 0.1 | 8.3 ± 0.1 | 8.5 ± 0.9 | 9.0 ± 1.0 | 8.0 ± 5.2 | 9.0 ± 5.2 | 9.1 ± 1.5 | 9.1 ± 1.5 |
| Week 12 | 4.1 ± 0.1 | 9.2 ± 0.6 | 9.2 ± 1.1 | 9.6 ± 0.7 | 8.8 ± 0.9 | 9.5 ± 0.8 | 9.5 ± 1.0 | 9.3 ± 0.9 |
| Week 24 | 3.7 ± 0.1 | 9.4 ± 01.3 | 9.4 ± 01.3 | 9.9 ± 1.1 | 9.0 ± 1.4 | 9.8 ± 1.2 | 9.8 ± 1.2 | 9.1 ± 1.2 |

(b) Survival: Compared with intravenous administration of STZ, intraperitoneal administration of STZ induced a less severe form of diabetes with lesser mortality rate. At the end of the 24 week study period, mortality rate amongst study animals was: Group 1, 0%; Group 2, 14.3%, Group 3, 0%; Group 4, 0%, Group 5, 0%; Group 6, 12.5%, Group 7, 0%, and Group 6, 0%. There was no significant difference between groups because of the low frequency of events.

(c) Weight gain: STZ diabetes caused a profound weight loss in diabetic rats compared with non-diabetic controls. Mean weight gain of study animals from the beginning to the end of the 24 week period are indicated in Table 6.

TABLE 6

|  | Group 1 | Group 2 | Group 3 | Group 4 | Group 5 | Group 6 | Group 7 | Group 8 |
|---|---|---|---|---|---|---|---|---|
| Mean ± SEM weight gain | 342.8 ± 13.7 | 54.4 ± 12.5 | 60.7 ± 20.7 | 33.7 ± 20.4 | 123.6 ± 20.5 | 56.1 ± 21.3 | 55.1 ± 17.1 | 75.8 ± 25.4 |
| P* | — | ns | ns | ns | 0.0138 | ns | ns | ns |

*Student's t test compared with untreated STZ rats (Group 2)

Triene administered alone (Group 5) caused a significant improvement on weight gain compared with the untreated STZ diabetic control rat group (Group 2). There was no evidence of synergy between classes of fructosamine oxidase inhibitors.

Triethylenetetramine dihydrochloride administered alone (Group 5) caused a significant improvement in weight gain compared with the untreated STZ diabetic control rat group (Group 2). There was no evidence of synergy between classes of fructosamine oxidase inhibitors.

(d) Cataract formation: Cataract formation has been a recognized long-term complication of poorly controlled diabetes. Gross cataract formation in STZ rats compared with diabetic control animals by the end of the study at week 24 is shown in Table 7.

TABLE 7

|  | Group 1 | Group 2 | Group 3 | Group 4 | Group 5 | Group 6 | Group 7 | Group 8 |
|---|---|---|---|---|---|---|---|---|
| No (%) with cataract | 0 (0%) | 8 (40%) | 2 (25%) | 2 (25%) | 0 (0%) | 2 (28%) | 5 (62%) | 1 (12%) |
| P* | — | — | ns | ns | <0.10 | ns | ns | ns |

*Chi-square test compared with diabetic control rats (Group 2)

Although not significant at the P=0.05 level, triethylenetetramine dihydrochloride appeared more effective than captopril and carbidopa in inhibiting gross cataract formation. There was no evidence of synergy between classes of fructosamine oxidase inhibitors.

(e) Diabetic cardiomyopathy: Cardiomyopathy has been a recognized long-term complication of poorly controlled diabetes. Macroscopically, hearts of STZ rats were dilated with thinning of the ventricular wall. Sections stained with hematoxylin and eosin and Masson's Trichrome showed focal pallor with a loss of normal architecture in the myocardium of both ventricles that began at the sub-endocardial and sub-epicardial regions and spread to encompass the whole ventricular wall in severely affected animals. There was also marked infiltration by fibrous connective tissue between myocytes and increased fibrous connective tissue in the walls of intramural arteries. These appearances were consistent with dilated cardiomyopathy. Gross myocardial fibrosis in STZ rats compared with non-diabetic control animals by the end of the study at week 24 is shown in Table 8.

TABLE 8

|  | Group 1 | Group 2 | Group 3 | Group 4 | Group 5 | Group 6 | Group 7 | Group 8 |
| --- | --- | --- | --- | --- | --- | --- | --- | --- |
| No (%) with severe fibrosis | 0 | 10 | 6 | 2 | 0 | 6 | 8 | 7 |
| P* | — | — | ns | ns | <0.005 | ns | <0.005 | ns |

*Chi-square test compared with diabetic control rats (Group 2)

Triethylenetetramine dihydrochloride was highly effective in inhibiting the development of diabetic cardiomyopathy. Diabetic cardiomyopathy causes histopathological and functional changes in the heart. The disease can be assessed post-mortem by examining the histology. Alternatively, the disease can be assessed ante-mortem by measuring heart function using echocardiography, cardiac catheter studies, or magnetic resonance imaging of the heart. There was no evidence of synergy between classes of fructosamine oxidase inhibitors.

(f) Clinical Pharmacokinetics:

Triethylenetetramine dihydrochloride. The bioavailability of triethylenetetramine dihydrochloride was less than 10%. Bioavailability refers to the degree to which a drug or other substance becomes available to the target tissue after administration. Bioavailability is usually expressed as that proportion of an administered dose that may be measured in the blood stream. See, for example, Kodama H. et al., Life Sci 61: 899-907 (1997). Most of the unchanged drug was cleared in the urine within the first 6 hours of oral dosing mainly as an acetyl derivative indicating that a three or four times daily drug regimen or a sustained release preparation was required. See, for example, Kodama H. et al. supra. In addition, plasma levels in non-fasted rats were significantly lower than those observed in fasted animals and the uptake of triethylenetetramine dihydrochloride from the intestinal brush border was competitively inhibited by other amine compounds. See, for example, Tanabe R. et al. J Pharm Pharmacol 48: 517-21 (1996). This implied that triethylenetetramine dihydrochloride was best administered in the fasting state. Fasting state was usually about half an hour before meals. Interference in the absorption of drug from the intestinal brush border could account for discrepancies between triethylenetetramine dihydrochloride treatment groups (Groups 5, 6, and 8). Finally, in the current study lasting approximately 6 months, each STZ rat consumed approximately 250 mL of water per day (12.5 mg triethylenetetramine dihydrochloride/rat/day). Assuming a mean body mass of 350 g, this dose of triethylenetetramine dihydrochloride equated to 35 mg/kg. The dose of triethylenetetramine dihydrochloride previously used in treating humans with another non-diabetic condition ranged between 1.2-2.4 g (17-35 mg/kg assuming a mean body mass 70 kg). See, Walshe J. M. Lancet 8273: 643-7 (1982). This implied that humans may be safely treated with comparable doses of trienes to those administered to rats in the current study to thereby elicit the fructosamine oxidase inhibition and/or antagonism advantages in a diabetic patient referred to herein.

Captopril. The bioavailability of captopril was approximately 65% after an oral dose. However, the drug was almost completely bound in vivo to albumin and other plasma proteins and formed inactive mixed disulfides with endogenous thiols so that plasma levels of active drug might have been very low. The elimination half life of unchanged captopril was approximately 2 hours. See, Duchin K. L. et al. Clin Pharmacokinet 14: 241-59 (1988). These observations might explain the reduced efficacy of captopril in the STZ rat compared with in vitro studies. Furthermore, each STZ rat consumed approximately 12.5 mg captopril/day which equated to 35 mg/kg assuming a mean body mass of 350 g. This dose far exceeded the maximum recommended human dose of 150 mg captopril per day (2 mg/kg assuming a mean body mass of 70 kg).

Carbidopa. In a study of beagle dogs, the oral absorption of carbidopa was almost complete and the absolute bioavailability was 88%. The biological half-life was 5 hours. See, for example, Obach R. et al. J Pharm Pharmacol 36: 415-6 (1984). However, carbidopa was an unstable compound and it degraded naturally in a short period. Solutions left to stand exposed to light at room temperature will undergo 50% oxidative degradation in 24 hours. See, for example, Pappert E. J. et al. Movement Disorders 12: 608-23 (1997). Reduced bioavailability due to oxidative degradation of the active drug both prior to its consumption and post-ingestion in the rat could explain (in part) the reduced efficacy of carbidopa in the current study. Finally, each STZ rat consumed approximately 12.5 mg carbidopa/day which equated to 35 mg/kg assuming a mean body mass of 350 g. This dose far exceeded the maximum recommended human dose of 200 mg carbidopa per day (3 mg/kg assuming a mean body mass of 70 kg).

Conclusions:

Intraperitoneal streptozocin was associated with a lower mortality rate than intravenous streptozocin in the rat.

Weight gain over a 6-month period was enhanced in STZ rats treated with the copper chelator triethylenetetramine dihydrochloride, as shown in Table 6. Captopril and carbidopa were ineffective.

Cataract development may be inhibited by a triene. Efficacy of triethylenetetramine dihydrochloride was diminished when the drug was co-administered with either captopril or carbidopa.

The development of diabetic cardiomyopathy was prevented by treatment with a triene. Triethylenetetramine dihydrochloride was administered in the amount of 50 mg of drug per liter in the drinking water. This amount resulted in an average dose of 12.5 mg triethylenetetramine dihydrochloride per rat per day based on an estimated water intake of 250 mL per day. In rat groups 6 and 8, triethylenetetramine dihydrochloride was mixed with captopril and carbidopa, respectively, in the drinking water. Concentrations of triethylenetetramine dihydrochloride, captopril, and carbidopa were all 50 mg of drug per liter of drinking water.

Efficacy of triethylenetetramine dihydrochloride was diminished when the drug was co-administered with either captopril or carbidopa (50 mg of drug per liter of drinking water).

Oral doses of a triene, triethylenetetramine dihydrochloride, which inhibited the development of complications in the rat (cataract, cardiomyopathy, and early death) were equivalent on a body mass basis to doses of triethylenetetramine dihydrochloride which had previously been used to treat human beings with another condition (not diabetes).

When administered to humans on a three or four times daily basis or as a sustained release preparation in previously tolerated doses of 1.2-2.4 g/day, triethylenetetramine dihydrochloride will provide an effective means of treating the long-term complications of diabetes mellitus.

Example 5

Double-Blind, Placebo-Controlled Clinical Trial

The purpose of this example is to demonstrate how the clinical usefulness of candidate fructosamine oxidase inhibitors is to be assessed in diabetic human subjects. A detailed protocol based on this proposal has been approved by the Auckland Regional Ethics Committee This approach takes into account drug bioavailability, the activity of the drugs and their metabolites, interactions between drugs, any drug adverse effects or toxicity factors and the "scale-up" factor from rat to human treatment.

Objective: This is a pilot study to determine whether a triene reduces the rate of progression of renal disease and associated microvascular complications in patients with diabetic nephropathy due to Type II diabetes mellitus.

Patient population: 60 men and women aged between 40 years and 70 years of age with poor blood glucose control and diabetic nephropathy due to Type II diabetes mellitus. Poor blood glucose control was defined as a hemoglobin $A_{1c}$ (Hb$A_{1c}$) greater than 7% in this group of patients with advanced microvascular complications, i.e., diabetic nephropathy. Diabetic nephropathy is a clinical syndrome defined as the patient having: (i) albuminuria greater than 300 mg per liter; (ii) plasma creatinine greater than 150 µmol per liter, and (iii) some evidence of diabetic retinopathy.

Study design and duration: Randomized double-blind, placebo-controlled study design consisting of five periods:

screening period (detecting possible candidates who meet study criteria);

enrolment period (securing informed consent and baseline measurements);

run-in period (trial of acceptability of study protocols and study medication);

maintenance period (treatment with drug/placebo, monitoring efficacy/safety);

follow-up period (detect any untoward effect when medication is discontinued).

Blinded therapy (a triene 400 mg or placebo) is administered three times daily {fraction (½)} hour before meals in addition to current anti-hypertensive and hypoglycemic therapies. The study terminates when all patients are randomized and have been in the study (maintenance period) for a minimum of 6 months. All randomized patients who discontinue study drug for any reason other than death are followed for the entire duration of the study; patients who undergo renal transplantation or dialysis are followed for vital status only.

Outcomes Efficacy:

The primary outcome measure consists of the rate of decline in renal function as measured by glomerular filtration rate (creatinine clearance). Creatinine clearance is a standard means of measuring renal function (glomerular filtration rate) in human subjects and since this procedure is a standard method and routine to a person of skill in the arts, no further definition or explanation is necessary.

The secondary outcome measures to be evaluated are development of diabetic retinopathy, diabetic peripheral neuropathy, and diabetic autonomic neuropathy.

Safety:

Safety parameters evaluated are adverse events and clinical laboratory abnormalities. Adverse events can be categorized as serious (i.e., life-threatening) or non-serious. Non-serious adverse events are any events, which the clinical investigator may consider to be secondary to the administration of the drug. Non-limiting examples include headache, nausea, cough, diarrhea, weight loss, alopecia, and impotence. Clinical laboratory abnormalities are assessed at time points by medical history, physical examination, and laboratory analyses and compared between groups. Non-limiting examples include anemia, thrombocytopenia, leukopenia, iron deficiency, disordered liver function tests, and impaired renal function tests.

Statistical considerations: The sample size estimate for this trial is determined for the primary hypothesis that the projected rate of decay of creatinine clearance (1 mL/min) in Type II diabetes mellitus patients with diabetic nephropathy (creatinine clearance <90 mL/min) is reduced by treating with a triene. The study is powered to detect (80%) a 6 mL/min change in creatinine clearance over 6 months with four 2-monthly readings (i.e., 0, 2, 4, and 6 months) assuming a 10% rate of loss to follow-up at the 5% significance level.

CONCLUSIONS

The efficacy of a triene as a treatment of microvascular complications in patients with Type II diabetes mellitus is confirmed.

The safety of long-term administration of a triene in patients with poor blood glucose control and diabetic nephropathy due to Type II diabetes mellitus is confirmed.

It also provides a means to determine the clinical usefulness of alternative fructosamine oxidase inhibitors such as the copper chelating compounds D-penicillamine, sar, and diamsar (i.e., triene could be used in place of placebo in ensuing clinical trials).

We claim:

1. A method of treating a human for diabetes, the method comprising administering to said human a composition comprising a therapeutically effective amount of a pharmaceutically acceptable cupric binding agent selected from the group consisting of triethylenetetramine dihydrochloride, penicillamine, sar, diamsar, and o-phenanthroline.

2. The method of claim 1 wherein said human has type 1 diabetes.

3. The method of claim 1 wherein said human has type 2 diabetes.

4. The method of any of claims 1, 2 or 3, wherein said cupric binding agent is a copper chelator.

5. The method of claim 4, wherein said copper chelator is administered orally.

6. A method of treating a human for diabetes, the method comprising administering to said human a composition comprising a therapeutically effective amount of a pharmaceutically acceptable oxidized copper binding agent.

7. The method of claim 1 wherein said human has type 1 diabetes.

8. The method of claim 1 wherein said human has type 2 diabetes.

9. The method of any of claims 6, 7, or 8, wherein said copper binding agent is a copper chelator.

10. The method of claim 9, wherein said copper chelator is administered orally.

11. A method of treating one or more long-term complications of diabetes in a human suffering therefrom, the method comprising administering a composition consisting essentially of a cupric binding agent in an amount effective to ameliorate one or more of said conditions.

12. The method of claim 11 wherein said human has type 1 diabetes.

13. The method of claim 11 wherein said human has type 2 diabetes.

14. The method of any of claims 11, 12 or 13, wherein said cupric binding agent is a copper chelator.

15. The method of claim 14, wherein said copper chelator is administered orally.

16. A method for minimizing or reducing tissue damage associated with diabetes mellitus in a human, which comprises the prophylactic administration to a human of a therapeutically effective amount of a cupric binding agent.

17. The method of claim 16 wherein said human has type 1 diabetes.

18. The method of claim 16 wherein said human has type 2 diabetes.

19. The method of any of claims 16, 17 or 18, wherein said cupric binding agent is a copper chelator.

20. The method of claim 19, wherein said copper chelator is administered orally.

21. A method of treating one or more long-term complications of diabetes in a human suffering therefrom, the method comprising administering a composition consisting essentially of a compound that can bind or chelate oxidized, copper in an amount effective to ameliorate one or more of said conditions.

22. The method of claim 21 wherein said human has type 1 diabetes.

23. The method of claim 21 wherein said human has type 2 diabetes.

24. The method of any of claims 21, 22, or 23, wherein said compound is a copper chelator.

25. The method of claim 21, wherein said copper chelator is administered orally.

26. A method for minimizing or reducing tissue damage associated with diabetes mellitus in a human, which comprises the prophylactic administration to a human of a therapeutically effective amount of a compound that can bind or chelate oxidized copper.

27. The method of claim 26 wherein said human has type 1 diabetes.

28. The method of claim 26 wherein said human has type 2 diabetes.

29. The method of any of claims 26, 27, 28, wherein said compound is a copper chelator.

30. The method of claim 29, wherein said copper chelator is administered orally.

31. A method of treating one or more long-term complications of diabetes in a human suffering therefrom, the method comprising forming a cupric complex within the human by administering a composition consisting essentially of an effective amount of a copper binding agent.

32. The method of claim 31 wherein said human has type 1 diabetes.

33. The method of claim 31 wherein said human has type 2 diabetes.

34. The method of any of claims 31, 32, or 33, wherein said copper binding agent is a copper chelator.

35. The method according to claim 34 wherein said copper chelator is administered orally.

36. A method of treating one or more long-term complications of diabetes in a human suffering therefrom, the method comprising forming an oxidized copper complex within the human by administering a composition consisting essentially of an effective amount of a copper binding agent.

37. The method of claim 36 wherein said human has type 1 diabetes.

38. The method of claim 36 wherein said human has type 2 diabetes.

39. The method of any of claims 36, 37, or 38, wherein said copper binding agent is a copper chelator.

40. The method according to claim 34 wherein said copper chelator is administered orally.

41. A method for minimizing or reducing tissue damage associated with diabetes mellitus in a human, the method comprising forming a cupric complex within the human by prophylactically administering an effective amount of a copper binding agent.

42. The method of claim 41 wherein said human has type 1 diabetes.

43. The method of claim 41 wherein said human has type 2 diabetes.

44. The method of any of claims 41, 42, or 43, wherein said copper binding agent is a copper chelator.

45. The method according to claim 44 wherein said copper chelator is administered orally.

46. A method for minimizing or reducing tissue damage associated with diabetes mellitus in a human, the method comprising forming an oxidized copper complex within the human by prophylactically administering an effective amount of a copper binding agent.

47. The method of claim 46 wherein said human has type 1 diabetes.

48. The method of claim 46 wherein said human has type 2 diabetes.

49. The method of any of claims 46, 47, or 48, wherein said copper binding agent is a copper chelator.

50. The method according to claim 49 wherein said copper chelator is administered orally.

* * * * *